United States Patent
Tagge et al.

(10) Patent No.: US 6,544,919 B1
(45) Date of Patent: Apr. 8, 2003

(54) MULTINUCLEAR TRANSITION METAL CATALYSTS FOR PREPARATION OF MULTIMODAL POLYMER COMPOSITIONS

(75) Inventors: Christopher D. Tagge, San Carlos, CA (US); Robert B. Wilson, Jr., Palo Alto, CA (US)

(73) Assignee: SRI International, Menlo Park, CA (US)

( * ) Notice: Subject to any disclaimer, the term of this patent is extended or adjusted under 35 U.S.C. 154(b) by 13 days.

(21) Appl. No.: 09/685,328

(22) Filed: Oct. 5, 2000

Related U.S. Application Data

(60) Provisional application No. 60/158,331, filed on Oct. 6, 1999.

(51) Int. Cl.$^7$ ............................ C08F 4/622; C08F 4/623

(52) U.S. Cl. ...................... 502/113; 502/117; 502/150; 502/155; 526/113; 526/114; 526/115; 526/117

(58) Field of Search .................................. 502/113, 117, 502/155, 150; 526/113, 114, 115, 117

(56) References Cited

U.S. PATENT DOCUMENTS

| | | | |
|---|---|---|---|
| 3,691,095 A | 9/1972 | Kroll et al. | |
| 4,659,685 A | 4/1987 | Coleman, III et al. | |
| 4,727,123 A * | 2/1988 | Weinert, Jr. et al. | 526/124 |
| 5,032,562 A | 7/1991 | Lo et al. | |
| 5,055,438 A | 10/1991 | Canich | |
| 5,459,117 A | 10/1995 | Ewen | |
| 5,525,678 A | 6/1996 | Mink et al. | |
| 5,557,023 A | 9/1996 | Somogyvari et al. | |
| 5,585,508 A | 12/1996 | Küber et al. | |
| 5,693,730 A | 12/1997 | Küber et al. | |
| 5,866,663 A * | 2/1999 | Brookhart et al. | 526/170 |
| 6,069,213 A * | 5/2000 | Nemzek et al. | 526/113 |
| 6,072,014 A * | 6/2000 | Wilson, Jr. | 526/352 |

FOREIGN PATENT DOCUMENTS

| | | |
|---|---|---|
| CA | 2175159 | 10/1996 |
| CA | 2192770 | 6/1997 |
| CA | 2192771 | 6/1997 |
| EP | 0416815 | 3/1991 |
| EP | 0739897 | 10/1996 |
| EP | 0779295 | 6/1997 |
| EP | 0779306 | 6/1997 |
| WO | WO 92/00333 | 1/1992 |
| WO | WO 97/48735 | 12/1997 |
| WO | WO 98/03521 | 1/1998 |
| WO | WO 98/27124 | 6/1998 |
| WO | WO 98/30612 | 7/1998 |
| WO | WO 98/40374 | 9/1998 |
| WO | WO 98/49208 | 11/1998 |
| WO | WO 98/12981 | 3/1999 |
| WO | WO 00/66600 | 11/2000 |

OTHER PUBLICATIONS

Desjardins et al. (1997), Single Component N–O Chelated Arylnickel(II) Complexes as Ethene Polymerisation and CO/Ethene Copolymerisation Catalysts. Examples of Ligand Induced Changes to the Reaction Pathway, *Journal of Organometallic Chemistry* 544:163–174.

Feldman et al. (1997), "Electrophilic Metal Precursors and a β–Diimine Ligand for Nickel(II)– and Palladium(II)–Catalyzed Ethylene Polymerization," *Organometallics* 16(8): 1514–1516.

Fujita et al. (1999), "Beyond Metallocenes: New Olefin Polymerization Catalysts with Exceptionally High Ethylene Polymerization Activity," *MetCon '99* Presentation, Houston, TX.

Hancock et al. (1976), "Bis(2,2'–Bipyridine) and Bis(1, 10–phenanthroline) Complexes of Chromium(III) and Cobalt(III)," *Acta Chemica Scandinavica A* 30(2):79–97.

Horton (1994), "Metallocene Catalysts: Polymers by Design?," *Trends Polym. Sci.* 2(5):158–166.

Johnson et al. (1995), "New Pd(II)–Based Catalysts for Polymerization of Ethylene and α–Olefins," *J. Am. Chem. Soc.* 117(23):6414–6415.

Johnson et al. (1996), "Copolymerization of Ethylene and Propylene with Functionalized Vinyl Monomers by Palladium(II) Catalysts," *J. Am. Chem. Soc.* 118(1):267–268.

Katayama et al. (1995), "The Effect of Aluminum Compounds in the Copolymerization of Ethylene / α–Olefins," *Macromol. Symp.* 97:109–118.

Kim et al. (1998), "[(Ph)$_2$nacnac]MCl$_2$(THF)$_2$ (M=Ti, V, Cr): A New Class of Homogeneous Olefin Polymerization Catalysts Featuring β–Diiminate Ligands," *Organometallics* 17(21):4541–4543.

Lindauer et al. (1995), "On the Aminolysis of Bis–Imidoyl-chlorides of Oxalic Acid. Part I. Reaction with ARomatic and Aliphatic Amines," *Journal of Für Praktische Chemie* 337:143–152.

Martinez–Martinez et al. (1993), "1H, 13C, 15N, 2D and Variable Temperature NMR Study of the Role of Hydrogen Bonding in the Structure and Conformation of Oxamide Derivatives," *J. Chem. Soc. Perkin Trans.* 2:1481–1485.

Wang et al. (1998), "Neutral Nickel(II)–Based Catalysts for Ethylene Polymerization," *Organometallics* 17(15):3149–3151.

(List continued on next page.)

Primary Examiner—David W. Wu
Assistant Examiner—R. Rabago
(74) Attorney, Agent, or Firm—Dianne E. Reed; Reed & Eberle LLP

(57) ABSTRACT

Novel compounds are provided that are useful as catalysts, particularly in the polymerization of addition polymerizable monomers such as olefinic or vinyl monomers. The compounds are multinuclear complexes of transition metals coordinated to at least one unsaturated nitrogenous ligand. Catalyst systems containing the novel compounds in combination with a catalyst activator are provided as well, as are methods of using the novel compounds in the preparation of polyolefins.

15 Claims, No Drawings

OTHER PUBLICATIONS

Weidenbruch et al. (1993), "L Reaktionen von Silylenen und Disilenen mit 2,2'–Bipyridyl, Pyridin–2–aldiminen und α–Ketoiminen: Cycloadditionen versus C–H–Insertion," *Journal of Organometallic Chemistry* 454:35–43.

Zuech (1972), "Polymerizations with Homogeneous Chromium Catalysts," *Journal of Polymer Science: Polymer Chemistry Edition* 10:3665–3672.

Britovsek et al. (1997), "Cationic Methyl–Palladium(II) Complexes Containing Bidentate N ^ O and P ^ O Ligands and a Tridentate P ^ O ^ N Ligand: Synthesis, Carbonylation and Catalytic Applications in the Copolymerisation of Carbon Monoxide and Ethene," *Journal of Organometallic Chemistry* 533:201–212.

Martin et al. (1998), "Neutral and Cationic Group 4 Metal Compounds Containing Octamethyldibenzotetraazaannulene ($Me_8taa^{2-}$) Ligands. Synthesis and Reactivity of ($Me_8taa)MX_2$ and $(Me_8taa)MX^+$ Copmlexes (M=Zr, Hf; X=Cl, Hydrocarbyl, $NR_2$, OR)," *Organometallics* 17(3):382–397.

Milani et al. (1985), "Catalytic Activity of Vanadium (III) and Oxovanadium(IV) Complexes in the Ziegler–Natta Synthesis of Ethylene–Propylene Elastomers," *Inorganica Chimica Acta* 103:15–18.

Po et al. (1998), "Polymerization of Styrene with Nickel Complex / Methylaluminoxane Catalytic Systems," *Journal od Polymer Science: Part A: Polymer Chemistry* 36:3119–2126.

Uflyand et al. (1986), "Effect of Structural Features of Nitrogen– and Oxygen–Containing Chelates of Cobalt(II) on Their Activity and Stereospecificity in the Butadiene Polymerization," *Koord. Khim.* 12(5):685–689 (abstract only).

Wöhrle et al. (1983), "Polymeric Schiff's Base Chelates and Their Precursors, $4^{a)}$—Syntheses of Schiff's Base Chelates from Diaminomaleonitrile and Investigation of Their Activity for the Valence Isomerisation of Quadricyclane to Norbornadien," *Makromol. Chem.* 184:763–778.

Ziessel (1998), "Molecular Tailoring of Organometallic Polymers for Efficient Catalytic $CO_2$ Reduction: Mode of Formation of the Active Species," *Advances in Chemical Conversions for Mitigating Carbon Dioxide, Studies in Surface Science and Catalysis* 114:219–224.

\* cited by examiner

MULTINUCLEAR TRANSITION METAL CATALYSTS FOR PREPARATION OF MULTIMODAL POLYMER COMPOSITIONS

CROSS-REFERENCE TO RELATED APPLICATIONS

This application claims priority to U.S. Provisional Patent Application Ser. No. 60/158,331, filed Oct. 6, 1999.

TECHNICAL FIELD

This invention relates generally to the field of catalysis, and more particularly relates to multinuclear complexes of transition metals and unsaturated nitrogenous ligands that are useful, inter alia, as polymerization catalysts. The invention additionally relates to methods for using the novel complexes as catalysts, particularly in the preparation of multimodal polymer products such as multimodal polyolefin compositions.

BACKGROUND

Many processes and catalysts are known for the preparation of homopolymeric or copolymeric olefins and other polymers. Ziegler-Natta catalyst compositions, developed in the 1950s, were found to be particularly useful in the preparation of polyolefins. These catalyst compositions comprise transition metal compounds such as titanium tetrachloride and an alkylaluminum (e.g., triethylaluminum) cocatalyst. The systems were found to be advantageous because of their high activity, and were largely consumed during polymerization.

Subsequent catalyst systems have been designed to provide more control over polymer structure and properties than could be achieved with Ziegler-Natta catalysts. These later catalysts have well-defined active sites and can be rationally designed to produce a specific polymer product, i.e., having predetermined structure and properties. Such catalysts include, for example, metal complexes known as "metallocenes." The term "metallocene" was initially coined in the early 1950s to refer to dicyclopentadienyliron, or "ferrocene," a structure in which an iron atom is contained between and associated with two parallel cyclopentadienyl groups. The term is now used to refer generally to organometallic complexes in which a metal atom (not necessarily iron) is coordinated to at least one cyclopentadienyl ring ligand. A. D. Horton, "Metallocene Catalysis: Polymers by Design," *Trends Polym. Sci.* 2(5):158–166 (1994), provides an overview of metallocene catalysts and their advantages, and focuses on now-conventional complexes of Group IV transition metal complexes and cyclopentadienyl ligands ($Cp_2MX_2$, wherein Cp represents a cyclopentadienyl ligand, M is Zr, Hf or Ti, and X is Cl or $CH_3$). Unfortunately, however, although metallocenes do provide significant advantages relative to the traditional Ziegler-Natta catalysts, the high cost and difficulties associated with heterogenization of metallocenes, as well as the oxophilic nature of the early transition metals, have limited the applicability of metallocenes as commercial polymerization catalysts.

Because polyolefins such as polyethylene and polypropylene are such important commercial polymers, there is an ongoing need for improved polymerization techniques and polymerization catalysts. Recently, researchers have developed new catalysts suitable for olefin polymerization that are complexes of late transition metals and substituted diimine ligands. Such catalysts are described, for example, in Bres et al., PCT Publication No. WO 98/49208, published Nov. 5, 1998. Other similar catalysts, comprised of diimine ligands and selected metals, are described in Bennett, PCT Publication No. WO 98/27174, published Jun. 25, 1998, and in Brookhart et al., PCT Publication No. WO 98/30612, published Jul. 16, 1998.

A variety of catalyst systems have been used in the creation of "multimodal" polymer compositions, i.e., compositions containing two or more molecular weight distributions as may be determined, for example, by the appearance of two or more peaks in a gel permeation chromatogram or the like. The term "multimodality" can also refer to other characteristics of a polymer composition as well, e.g., compositional distribution (the distribution of comonomers within a copolymer), tacticity distribution (wherein a polymer composition contains at least two segments of differing tacticity, long-chain branching distribution, and the like. Such multimodal polymers are frequently more useful than compositions that are not; for example, multimodal polymer compositions can have improved rheological behavior, higher mechanical strength and increased elasticity relative to corresponding compositions that are not multimodal.

Several processes are known for preparing multimodal polymer compositions using the catalyst systems discussed above. In U.S. Pat. No. 5,032,562 to Lo et al., a process involving the use of tandem reactors operated in series is described wherein, in a first reactor, an olefinic monomer is catalytically polymerized in the presence of hydrogen, with the product then transferred to a second reactor in which polymerization is conducted in the presence of hydrogen. In this way, a higher molecular weight polymer is produced in the first reactor, and the lower molecular weight polymer is produced in the second reactor.

U.S. Pat. No. 5,525,678 to Mink et al. provides a supported catalyst composition for producing a polyolefin resin having a high molecular weight component and a low molecular weight component, wherein the catalyst composition contains a first catalyst that is a metallocene and a second catalyst that is a non-metallocene. The ratio of the high molecular weight and low molecular weight components in the polymeric product is determined by the ratio of the concentration of the two metals in the two-component catalyst composition. In addition, U.S. Pat. No. 4,659,685 to Coleman, III et al. Describes a two-component catalyst composition for preparing polyolefins having a molecular weight distribution which is multimodal, the catalyst composition comprising a mixture of a supported titanium compound and a separately supported or non-supported organometallic compound.

U.S. Pat. No. 5,032,562 to Lo et al., cited above, also relates to a supported olefin polymerization catalyst composition for producing high density polyethylene ("HDPE") having a multimodal molecular weight distribution. The catalyst composition comprises: (1) a catalyst precursor supported on a porous carrier, and (2) a catalyst activator in the form of a mixture of conventional Ziegler-Natta cocatalysts. Katayama et al., "The Effect of Aluminum Compounds in the Copolymerization of Ethylene/α-Olefins," in *Macromol. Symp.* 97:109–118 (1995), describes a similar system for preparing a polymer composition having a bimodal composition using a two-component catalyst comprised of a metallocene ($CP_2ZrCl_2$) and either $[Ph_3C^+][B(C_6F_5)_4^-]$ or $[PhMe_2NH^+][B(C_6F_5)_4^-]$.

PCT Publication No. WO 92/00333, inventors Canich et al., and EP 416,815, inventors Stevens et al., are also of interest insofar as the references describe metallocene catalysts for preparing polyolefins. Canich et al. describes metallocene catalyst compositions for producing high molecular weight polyolefins having a relatively narrow molecular weight distribution, wherein the catalyst composition is comprised of (1) a metallocene containing a Group IVB transition metal coordinated to a cyclopentadienyl ligand, and (2) a coordination complex such as an anionic complex containing a plurality of boron atoms, which serves as a catalyst activator. The metallocene catalysts described may be monoriuclear or binuclear (i.e., containing one or two metal atoms which serve as the active sites); the binuclear compounds dissociate during polymerization. Stevens et al. also pertains to metallocene catalysts to prepare addition polymers, particularly homopolymers and copolymers of olefins, diolefins, "hindered" aliphatic vinyl monomers and vinylidene aromatic monomers. The Stevens et al. catalysts are metal coordination complexes having constrained geometry, and are used in conjunction with a cocatalyst compound to form a complete catalytic system. The constrained geometry of the catalysts is stated to be of key importance insofar as the metal atom in the metallocene presumably is a more "exposed" active site.

Thus, the art provides metallocene catalyst compositions for producing polymers, particular polyolefins, that have a multimodal molecular weight distribution. However, such prior catalysts and catalyst compositions either require two or more components, e.g., two catalysts used in combination, or involve binuclear compounds that break apart into two separate components during the polymerization process (as in the bimetallic catalyst disclosed by Canich et al.), giving rise to potential manufacturing problems, e.g., phase separation or the like, and/or loss of control over the molecular weight distribution of the polymer composition prepared. In addition, the known metallocene catalysts can be relatively difficult and time-consuming to synthesize, requiring expensive equipment, extreme reaction conditions, and multi-step processes that ultimately result in a low yield of the desired product.

Accordingly, there is a need in the art for a simpler way of catalytically preparing multimodal polymer compositions while avoiding the high cost and difficulties associated with prior processes. An ideal method for preparing a multimodal polymeric product would involve a single catalyst that does not require the presence of a second catalyst, that retains its structure during the polymerization process, and is relatively simple to synthesize. The present invention is directed to such a catalyst.

The novel catalyst is comprised of an organometallic complex having two or more different active sites, at least one of which is composed of a transition metal atom coordinated to an unsaturated nitrogenous compound such as an imine, diimine or a 2,2'-bipyridine-containing compound. Use of such catalysts provide numerous advantages relative to the multimodal polymerization catalyst of the prior art, in that they:

1) allow for a exceptional control over the final polymer composition;
2) produce uniform multimodal products;
3) can be constructed via a straightforward, low cost synthesis;
4) are highly active polymerization catalysts;
5) can be used to catalyze reactions other than polymerization reactions, e.g., hydrogenation
6) enable preparation of commodity polymers such as linear low density polyethylene and isotactic polypropylene;
7) can be used as either supported or homogeneous polymerization catalysts;
8) are quite versatile and can be used in conjunction with a variety of monomer types; and
9) provide for all of the advantages typically associated with metallocene catalysts, i.e., versatility and use in conjunction with a variety of monomer types, the ability to control the degree of vinyl unsaturation in the polymeric product, and the like.

The invention thus represents a significant advance in the field of catalysis, as prior to the development of the catalysts disclosed and claimed herein, only a few of the aforementioned advantages could be achieved with a single catalyst system.

SUMMARY OF THE INVENTION

Accordingly, it is a primary object of the invention to provide a compound useful as a polymerization catalyst having two or more different active sites, at least one of which is comprised of a metal atom coordinated to an unsaturated nitrogenous ligand such as an imine, diimine or a 2,2'-bipyridine-containing compound.

It is a further object of the invention to provide a catalyst system which utilizes such a compound.

It is a further object of the invention to provide such compounds which are useful for preparing polyolefins or other polymers deriving from the polymerization of addition polymerizable monomers containing one or more degrees of unsaturation.

It is a still further object of the invention to provide a method for making an array of such compounds.

Additional objects, advantages and novel features of the invention will be set forth in part in the description which follows, and in part will become apparent to those skilled in the art upon examination of the following, or may be learned by practice of the invention.

In a first embodiment, then, novel compounds are provided comprised of multinuclear organometallic complexes, i.e., complexes having at least two active sites and associated organic ligands. The active sites have transition metal centers. The complex comprises an unsaturated nitrogenous compound, e.g., an imine, diimine or a 2,2'-bipyridine-containing compound, chelating the first transition metal center, with a second transition metal center chelated with either a second unsaturated nitrogenous compound or a cyclopentadienyl ligand. Additional metal centers may be present as well. Examples of suitable unsaturated nitrogenous ligands are those that contain a first coordinating atom that is a nitrogen atom contained within a C=N group, and a second coordinating atom that is either a second nitrogen atom, that may or may not be present in a second C=N group, or an oxygen, sulfur or phosphorus atom.

In another embodiment, the novel compounds are organometallic complexes comprising a first active site comprised of a transition metal atom $M^1$, and an unsaturated nitrogenous ligand having the structure of formula (I)

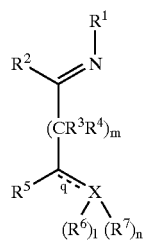

(I)

and a second active site comprised of a metal atom $M^2$, wherein $M^2$ is coordinated either to an unsaturated nitrogenous ligand having the structure of formula (I) or to one or more cyclopentadienyl moieties (II)

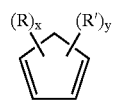

(II)

wherein:
q is an optional double bond;
X is N, O, S or P, with the provisos that (a) when X is N or P, then either n is 1 or q is present as a double bond, but not both, and (b) when X is O or S, then n is zero and q is absent;
$R^1$, $R^6$, and $R^7$ are independently hydrido, hydrocarbyl or substituted hydrocarbyl, and $R^2$ and $R^5$ are independently hydrido, halo, hydrocarbyl or substituted hydrocarbyl, or $R^1$ and $R^2$ and/or $R^5$ and $R^6$ may be taken together to form a linkage —Q*—, resulting in a five- or six-membered cyclic group, wherein Q* is —[(CR*)$_{a*}$(Z)$_{b*}$]— in which a* is 2, 3 or 4, Z is N, O or S, b* is zero, 1 or 2, the sum of a* and b* is 3 or 4, and R* is selected from the group consisting of hydrido, halo, hydrocarbyl, hydrocarbyloxy, trialkylsilyl, $NR^8_2$, $OR^9$, and $NO_2$ wherein $R^8$ and $R^9$ are each independently hydrocarbyl, or wherein R* moieties on adjacent carbon atoms may be linked to form an additional five- or six-membered ring, or $R^2$ and $R^5$ may together form a linkage —Q*— as just defined;
$R^3$ and $R^4$ are independently selected from the group consisting of hydrido and hydrocarbyl;
l is zero or 1;
m and n are independently zero or 1, preferably both zero; and
R and R' are independently selected from the group consisting of halogen, $C_1$–$C_{24}$ hydrocarbyl, $C_1$–$C_{24}$ hydrocarbyl substituted with one or more halogen atoms, and $C_1$–$C_{24}$ hydrocarbyl-substituted Group IVB elements, x is 0, 1, 2, 3 or 4, and y is 0, 1, 2, 3 or 4, with the proviso that the sum of x and y cannot exceed 4, or, when R and R' are ortho to each other and x and y are each 1 or greater, R and R' they can together form a five- or six-membered cyclic structure optionally substituted with one to four substituents selected from the group consisting of halogen, $C_1$–$C_{24}$ hydrocarbyl, $C_1$–$C_{24}$ hydrocarbyl substituted with one or more halogen atoms, and $C_1$–$C_{24}$ hydrocarbyl-substituted Group IVB elements.

In general, the aforementioned organic complexes may be represented by the structural formula (III)

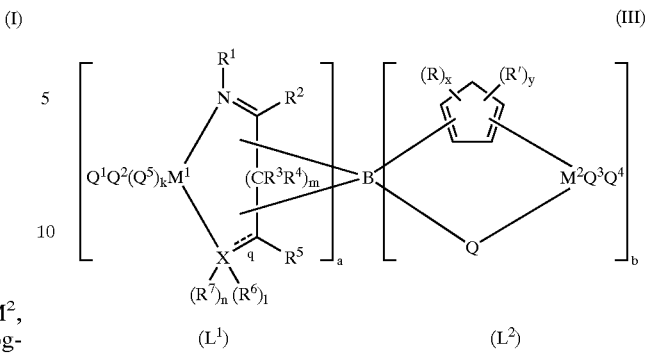

(III)

wherein:
B is a covalent bridging group comprising carbyl, silyl, disilyl, germanyl, ammonium, phosphonium,

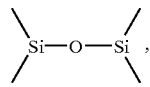

or a $C_1$–$C_{30}$ hydrocarbylene, substituted hydrocarbylene, heterohydrocarbylene or substituted heterohydrocarbylene radical optionally containing a Group IVB element, a Group VB element, or both a Group IVB element and a Group VB element, and is capable of binding up to $n_{max}$ substituents through single covalent bonds, wherein $n_{max}$ is at least 4;
$R^1$, $R^2$, $R^3$, $R^4$, $R^5$, $R^6$, $R^7$, X, 1, m, n and q are as defined above with respect to formula (I), and R, R', x and y are as defined above with respect to formula (II);
$Q^1$, $Q^2$, $Q^3$ and $Q^4$ are independently selected from the group consisting of univalent radicals;
$Q^5$ is an optional ligand having the structure of formula (I);
The subscript k is zero or 1;
$M^1$ is a transition metal;
$M^2$ is a Group IIIA element, a Group IVA element, a Group VA element, a lanthanide, or an actinide;
Q is cyclopentadienyl, indenyl, fluorenyl, indolyl, aminoboratobenzyl, unsubstituted or substituted with R and/or $R^1$ substituents as above, or Q may be $J(R^x)_{z-2}$ wherein J is an element with a coordination number of three from Group VB or an element with a coordination number of two from Group VIB, $R^x$ is selected from the group consisting of hydrogen, $C_1$–$C_{24}$ hydrocarbyl, $C_1$–$C_{24}$ hydrocarbyl substituted with one or more halogen atoms, and $C_1$–$C_{24}$ alkoxy, and z is the coordination number of J, and further wherein Q substituents on different Z groups are linked through a $C_1$–$C_{30}$ hydrocarbylene bridge,
a is at least 1, b is 0, 1 or 2, and the sum of a and b is 2 or 3.

The complex may also contain additional $BL^1$ and/or $BL^2$ moieties.

In a related embodiment, the novel compounds are organometallic complexes comprising a first active site comprised of a transition metal atom $M^1$ and a 2,2'-bipyridine-containing ligand having the structure of formula (IV)

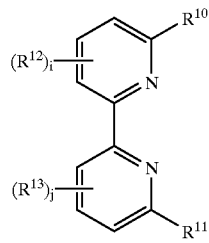

(IV)

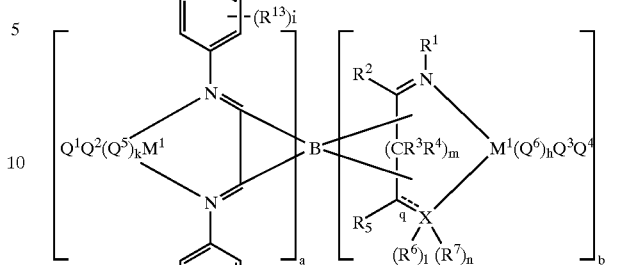

(VIII)

and a second active site comprised of either a metal atom $M^2$, wherein $M^2$ is coordinated to one or more cyclopentadienyl ligands of formula (II), or a transition metal atom $M^1$, wherein $M^1$ is coordinated to an unsaturated nitrogenous ligand having the structure of formula (I), i and j are independently zero, 1, 2 or 3, and $R^{10}$, $R^{11}$, $R^{12}$ and $R^{13}$ are independently hydrido, hydrocarbyl or substituted hydrocarbyl.

In general, the aforementioned organic complexes may be represented by the structural formulas (V), (VI), (VII), (VIII) and (IX)

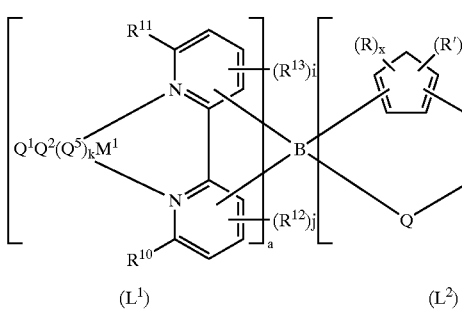

(V)

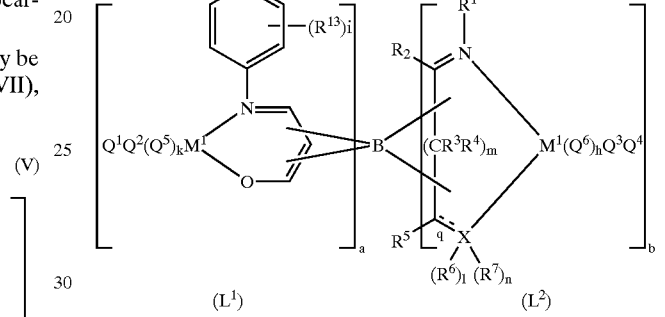

(IX)

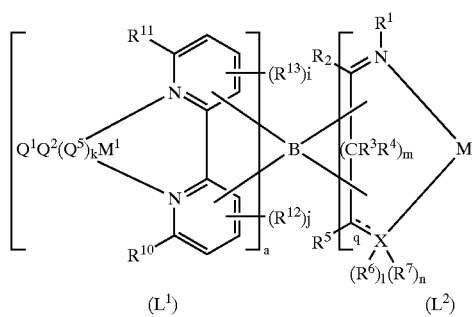

(VI)

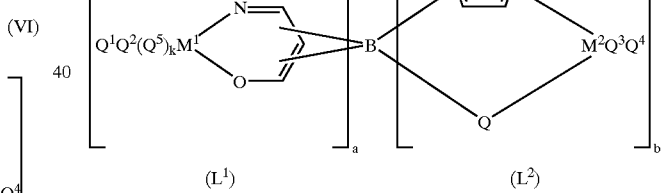

(X)

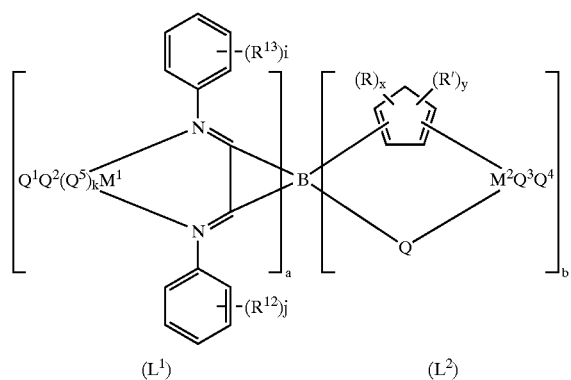

(VII)

wherein $R^1$, $R^2$, $R^3$, $R^4$, $R^5$, $R^6$, $R^7$, X, l, m, n and q, are as defined above with respect to formula (I), R, R', x and y are as defined above with respect to formula (II), and a, b, $M^1$, $M^2$, Q. $Q^1$, $Q^2$ $Q^3$ and $Q^4$ are as defined above with respect to formula (III);

$Q^5$ and $Q^6$ are optional ligands having the structure of formula (I); and k and h are independently zero or 1;

These complexes may also contain additional $BL^1$ and/or $BL^2$ moieties.

In another embodiment of the invention, a catalyst system is provided comprised of (1) a compound of the invention, as a catalyst, and (2) a catalyst activator, typically an aluminum-containing or boron-containing material. An exemplary catalyst is activator is methyl aluminoxane ("MAO"). When used in catalyzing polymerization, the catalyst system will be combined with an inert diluent, e.g., a hydrocarbon solvent, and optional additives such as polymerization rate accelerators.

An additional embodiment of the invention provides a method for preparing an polymer utilizing the catalyst system of the invention. The method comprises contacting selected addition polymerizable monomers having at least one degree of unsaturation with the inventive catalyst system under polymerization conditions effective to provide the desired polymer composition or other product.

With respect to the preparation of polyolefins, such polymers, as is known in the art, can be prepared having a variety of steric configurations deriving from the manner in which each monomer is added to the growing polymer chain. Four basic configurations are commonly recognized for polyolefins: atactic, in which monomer orientation is random; isotactic, in which each monomer is incorporated into the polymer in the same configuration; syndiotactic, in which the configuration of monomers alternates along a polymer chain; and hemi-isotactic, in which unique and regularly repeating stereochemistries are present within a single polymer chain. The present catalysts are useful for preparing polymers of desired tacticity, insofar as chiral catalysts can be used to catalyze stereospecific polymerization. Generally, a transition metal center having $C_2$ symmetry will give rise to isotactic polymers, while those catalysts having $C_s$ symmetry will give rise to syndiotactic polymers.

In addition to their utility as polymerization catalysts, the novel compounds are also useful in catalyzing other types of reactions, e.g., hydrogenation, dehydrocoupling, cyclization, substitution, carbomagnesation and hydrosilylation.

DETAILED DESCRIPTION OF THE INVENTION

Definitions and Nomenclature

Before the present compounds, compositions and methods are disclosed and described, it is to be understood that unless otherwise indicated this invention is not limited to specific molecular structures, ligands, or the like, as such may vary. It is also to be understood that the terminology used herein is for the purpose of describing particular embodiments only and is not intended to be limiting.

It must be noted that, as used in the specification and the appended claims, the singular forms "a," "an" and "the" include plural referents unless the context clearly dictates otherwise. Thus, for example, reference to "a substituent" includes one or more substituents, reference to "a ligand" includes one or more ligands, and the like.

The term "alkyl" as used herein refers to a branched or unbranched saturated hydrocarbon group of 1 to approximately 24 carbon atoms, typically 1 to approximately 12 carbon atoms, such as methyl, ethyl, n-propyl, isopropyl, n-butyl, isobutyl, t-butyl, octyl, decyl, tetradecyl, hexadecyl, eicosyl, tetracosyl and the like, as well as cycloalkyl groups such as cyclopentyl, cyclohexyl and the like. The term "lower alkyl" intends an alkyl group of 1 to 6 carbon atoms, preferably 1 to 4 carbon atoms.

The term "alkylene" as used herein refers to a difunctional saturated branched or unbranched hydrocarbon chain containing from 1 to approximately 24 carbon atoms, typically 1 to approximately 12 carbon atoms, and includes, for example, methylene (—CH$_2$—), ethylene (—CH$_2$—CH$_2$—), propylene (—CH$_2$—CH$_2$—CH$_2$—), 2-methylpropylene (—CH$_2$—CH(CH$_3$)—CH$_2$—), hexylene (—(CH$_2$)$_6$—), and the like. "Lower alkylene" refers to an alkylene group of 1 to 6, more preferably 1 to 4, carbon atoms.

The term "alkenyl" as used herein refers to a branched or unbranched hydrocarbon group of 2 to approximately 24 carbon atoms, typically 2 to approximately 12 carbon atoms, containing at least one carbon-carbon double bond, such as ethenyl, n-propenyl, isopropenyl, n-butenyl, isobutenyl, t-butenyl, octenyl, decenyl, tetradecenyl, hexadecenyl, eicosenyl, tetracosenyl and the like. Preferred alkenyl groups herein contain 2 to 12 carbon atoms and 2 to 3 carbon-carbon double bonds. The term "lower alkenyl" intends an alkenyl group of 2 to 6 carbon atoms, preferably 2 to 4 carbon atoms, containing one —C═C— bond. The term "cycloalkenyl" intends a cyclic alkenyl group of 3 to 8, preferably 5 or 6, carbon atoms.

The term "alkenylene" refers to a difunctional branched or unbranched hydrocarbon chain containing from 2 to approximately 24 carbon atoms, typically 2 to approximately 12 carbon atoms, and at least one carbon-carbon double bond. "Lower alkenylene" refers to an alkenylene group of 2 to 6, more preferably 2 to 5, carbon atoms, containing one —C═C— bond.

The term "alkynyl" as used herein refers to a branched or unbranched hydrocarbon group of 2 to approximately 24 carbon atoms, as above containing at least one —C≡C— bond, such as ethynyl, n-propynyl, isopropynyl, n-butynyl, isobutynyl, t-butynyl, octynyl, decynyl and the like. Preferred alkynyl groups herein contain 2 to 12 carbon atoms. The term "lower alkynyl" intends an alkynyl group of 2 to 6, preferably 2 to 4, carbon atoms, and one —C≡C— bond.

The term "alkynylene" refers to a difunctional branched or unbranched hydrocarbon chain containing from 2 to approximately 24 carbon atoms as before and at least one carbon-carbon triple bond. "Lower alkynylene" refers to an alkynylene group of 2 to 6, more preferably 2 to 5, carbon atoms, containing one —C≡C— bond.

The term "alkoxy" as used herein intends an alkyl group bound through a single, terminal ether linkage; that is, an "alkoxy" group may be defined as —OR where R is alkyl as defined above. A "lower alkoxy" group intends an alkoxy group containing one to six, more preferably one to four, carbon atoms.

The term "array" used herein refers to a regular, orderly, two or three dimensional arrangements of compounds. Arrays typically comprise from 2 to 1,000,000,000 features.

The term "aryl" as used herein refers to an aromatic species containing 1 to 5 aromatic rings, either fused or linked, and either unsubstituted or substituted with 1 or more substituents typically selected from the group consisting of —(CH$_2$)$_x$—NH$_2$, —(CH$_2$)$_x$—COOH, —NO$_2$, halogen, alkyl, alkenyl, alkynyl, alkoxy, alkenyloxy, alkynyloxy, alkylthio, aryl, aralkyl, and the like, where x is an integer in the range of 0 to 6 inclusive as outlined above. Preferred aryl substituents contain 1 to 3 fused aromatic rings, and particularly preferred aryl substituents contain 1 aromatic ring or 2 fused aromatic rings. The terms "aralkyl" and "alkaryl" refer to moieties containing both alkyl and aryl species, typically containing less than about 24 carbon atoms, and more typically less than about 12 carbon atoms in the alkyl segment of the moiety, and typically containing 1 to 5 aromatic rings. The term "aralkyl" refers to aryl-substituted alkyl groups, while the term "alkaryl" refers to alkyl-substituted aryl groups. The terms "aralkylene" and "alkarylene" are used in a similar manner to refer to aryl-substituted alkylene and alkyl-substituted arylene moieties.

The term "arylene" refers to a difunctional aromatic moiety; "monocyclic arylene" refers to a cyclopentylene or phenylene group. These groups may be substituted with up to four ring substituents as outlined above.

The term "heterocyclic" refers to a five- or six-membered monocyclic structure or to an eight- to eleven-membered bicyclic structure which is either saturated or unsaturated. Each heterocycle consists of carbon atoms and from one to four heteroatoms selected from the group consisting of nitrogen, oxygen and sulfur. As used herein, the terms "nitrogen heteroatoms" and "sulfur heteroatoms" include any oxidized form of nitrogen and sulfur, and the quaternized form of any basic nitrogen. Examples of heterocyclic groups include piperidinyl, pyrazinyl, morpholinyl and pyrrolidinyl.

"Halo" or "halogen" refers to fluoro, chloro, bromo or iodo, and usually relates to halo substitution for a hydrogen atom in an organic compound. Of the halos, chloro and fluoro are generally preferred.

"Hydrocarbyl" refers to univalent hydrocarbyl radicals containing 1 to about 30 carbon atoms, preferably 1 to about 20 carbon atoms, most preferably 1 to about 12 carbon atoms, including branched or unbranched, saturated or unsaturated species, such as alkyl groups, alkenyl groups, aryl groups, and the like. The term "lower hydrocarbyl" intends a hydrocarbyl group of 1 to 6 carbon atoms, preferably 1 to 4 carbon atoms. The term "hydrocarbylene" intends a divalent hydrocarbyl moiety containing 1 to about 30 carbon atoms, preferably 1 to about 24 carbon atoms, most preferably 1 to about 12 carbon atoms, including branched or unbranched, saturated or unsaturated species, or the like. The term "lower hydrocarbylene" intends a hydrocarbylene group of one to six carbon atoms, preferably one to four carbon atoms. "Substituted hydrocarbyl" refers to hydrocarbyl substituted with one or more substituent groups, and the terms "heteroatom-containing hydrocarbyl" and "heterohydrocarbyl" refer to hydrocarbyl in which at least one carbon atom is replaced with a heteroatom. Similarly, "substituted hydrocarbylene" refers to hydrocarbylene substituted with one or more substituent groups, and the terms "heteroatom-containing hydrocarbylene" and "heterohydrocarbylene" refer to hydrocarbylene in which at least one carbon atom is replaced with a heteroatom.

By "substituted" as in "substituted hydrocarbyl" or "substituted hydrocarbylene" is meant that the hydrocarbyl or hydrocarbylene group contains one or more substituent groups which are inert under the process conditions to which the compound containing these groups is subjected. "Monosubstituted" refers to a hydrocarbyl or hydrocarbylene group having one substituent group and "disubstituted" refers to a hydrocarbyl or hydrocarbylene group containing two substituted groups. The substituent groups also do not substantially interfere with the process. Included in the meaning of "substituted" are heteroaromatic rings. Examples of substituents include, but are not limited to, amino (including primary amino and alkyl-substituted, typically lower alkyl-substituted, secondary and tertiary amino), alkyl (typically lower alkyl), alkoxy (typically lower alkoxy), alkenyl (typically lower alkenyl), aryl (e.g., phenyl), halo, haloalkyl, imino, nitro, and the like.

A "substrate" refers to a material having a rigid or semi-rigid surface. In some embodiments, at least one surface of the substrate will be substantially flat. In other embodiments, the substrate will be divided into physically separate synthesis regions. Division of the substrate into physically separate synthesis regions can be achieved with, for example, dimples, wells, raised regions, etched trenches, or the like. In some embodiments, small beads or pellets may be provided on the surface by, for example, placing the beads within dimples, wells or within or upon other regions of the substrate's surface. Alternatively, the small beads or pellets may themselves be the substrate. An appropriate substrate can be made out of any material which is compatible with the process intended to occur thereon. Such materials include, but are not limited to, organic and inorganic polymers, quartz, glass, silica, etc. The choice of an appropriate substrate for certain given conditions will be apparent to those of skill in the art.

The term "synthesis support" as used herein refers to a material such as, for example, silica, alumina, a resin or controlled pore glass (CPG) which is functionalized to allow a ligand or a ligand component to be attached either reversibly or irreversibly there to. A synthesis support can be held within or upon a "substrate." "Synthesis support," "support," "bead," and "resin" are used interchangeably herein.

The term "unsaturated nitrogenous compound" refers to a compound having a C=N moiety. Unsaturated nitrogenous compounds herein include both a true imine wherein the C=N moiety is present in an acyclic molecular segment, as well as nitrogenous heterocycles in which the carbon-nitrogen bond is present in an aromatic ring, e.g., as in pyridine, pyrimidine, pyrazine, and the like.

"Optional" or "optionally" means that the subsequently described event or circumstance may or may not occur, and that the description includes instances where said event or circumstance occurs and instances where it does not. For example, the phrase "optionally substituted hydrocarbyl" means that a hydrocarbyl moiety may or may not be substituted and that the description includes both unsubstituted hydrocarbyl and hydrocarbyl where there is substitution.

A "heterogeneous" catalyst as used herein refers to a catalyst which is supported on a carrier, typically although not necessarily a substrate comprised of an inorganic, solid, particulate porous material such as silicon and/or aluminum oxide.

A "homogeneous" catalyst as used herein refers to a catalyst which is not supported but is simply admixed with the initial monomeric components in a suitable solvent.

By "stereospecific" is meant a catalyst that will provide a polymer of predetermined, desired stereoregularity. The preferred catalysts herein are "stereospecific." By "isospecific" is meant a catalyst that will provide an isotactic polymer. By "syndiospecific" is meant a catalyst that will provide a syndiospecific polymer. The most preferred catalysts herein are "isospecific" and "syndiospecific."

The term "multimodal molecular weight distribution" as used herein, and as alluded to above, refers to a polymer composition having two or more molecular weight distributions, as may be determined, for example, by the appearance of two or more peaks in a gel permeation chromatogram. Unless otherwise specified herein, the term "multimodal" is intended to encompass the term "bimodal." By the process of the invention, polymer compositions having a "multimodal" molecular weight distribution can be generated using a multinuclear complexes of transition metals coordinated to at least one unsaturated nitrogenous ligand, in which polymerization takes place at different propagation rates at different active sites within the catalyst structure, or wherein the different active sites give rise to different termination rates, and/or wherein the different active sites have different responses to $H_2$ (or other chain transfer agents). While the term "multimodality" generally refers to a multimodal molecular weight distribution, it should be emphasized that a polymer composition can also be "multimodal" with respect to compositional distribution, tacticity distribution, long-chain branching distribution, or the like.

As used herein all reference to the Periodic Table of the Elements and groups thereof is to the version of the table published by the Handbook of Chemistry and Physics, CRC Press, 1995, which uses the IUPAC system for naming groups.

The Novel Compounds

In a first embodiment, then, the novel compounds can be generally represented by the formula. $(L^1)_a B(L^2)_b$. They compounds are multinuclear organometallic complexes, i.e., complexes having at least two active sites and associated organic ligands. The complexes comprise an unsaturated nitrogenous ligand chelating a first transition metal center, with a second metal center chelated with either an unsaturated nitrogenous ligand or a cyclopentadienyl-based ligand. Additional metal centers may be present as well, along with additional unsaturated nitrogenous ligands and/or cyclopentadienyl-based ligands. Unsaturated nitrogenous ligands contain a first coordinating atom that is a nitrogen atom contained within a C=N group, and a second coordinating atom that is either a second nitrogen atom, which may or may not be present in a second C=N group, or an oxygen, sulfur or phosphorus atom. Each C=N group may be a true imine functionality contained within an acyclic molecular segment, or may represent a linkage within a heterocycle such as a pyridine or pyrimidine ring.

Exemplary complexes are represented by structural formula (III)

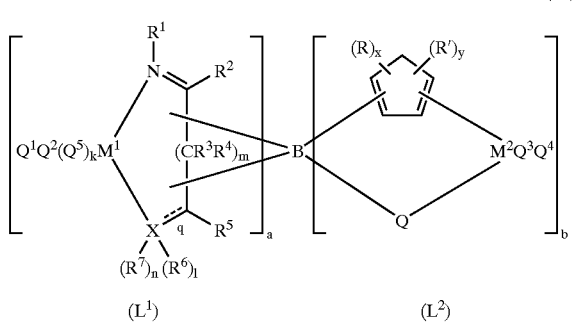

(III)

wherein:

B is a covalent bridging group comprising carbyl, silyl, disilyl, germanyl, ammonium, phosphonium,

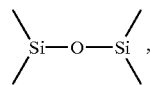

or a $C_1-C_{30}$ hydrocarbylene, substituted hydrocarbylene, heterohydrocarbylene or substituted heterohydrocarbylene radical optionally containing a Group IVB element, a Group VB element, or both a Group IVB element and a Group VB element, and is capable of binding up to $n_{max}$ substituents through single covalent bonds, wherein $n_{max}$ is at least 4. Preferred B groups are $C_1-C_{30}$ hydrocarbylene, substituted hydrocarbylene, heterohydrocarbylene or substituted heterohydrocarbylene radicals optionally containing a Group IVB element and/or a Group VB element, and particularly preferred B groups are aryl $C_1-C_{30}$ heterohydrocarbylene groups, and silicon.

The cyclopentadienyl moiety, as shown, is optionally substituted with R and R' groups. Specifically, the integers x and y are independently 0, 1, 2, 3 or 4, with the proviso that the sum of x and y cannot exceed 4; preferably, x and y are independently 0, 1 or 2, and most preferably are 0 or 1. R and R' can be halogen, $C_1-C_{24}$ hydrocarbyl, either unsubstituted or substituted with one or more halogen atoms, lower alkyl groups and/or Group IVB elements. Alternatively, when an R and an R' substituent are both present, and ortho to each other on the cyclopentadienyl ring, they may together form a five- or six-membered cyclic structure. This cyclic structure may be unsubstituted or substituted with a halogen or $C_1-C_{24}$ hydrocarbyl group as explained above. Preferred R and R' substituents are halogen and $C_1-C_2$ alkyl; complexes wherein R and R' are ortho to each other and linked to form a cyclopentadienyl or indenyl group, either unsubstituted or substituted with halogen and/or lower alkyl moieties, are also preferred. Particularly preferred R and R' groups are halogen and lower alkyl; complexes wherein R and R' are ortho to each other and linked to form a cyclopentadienyl ring optionally substituted with a lower alkyl group are also particularly preferred.

Q is cyclopentadienyl, indenyl, fluorenyl, indolyl or aminoboratobenzyl, and may be unsubstituted or substituted with R and/or $R^1$ substituents as above. Alternatively, Q is $J(R^x)_{z-2}$ wherein J is an element with a coordination number of three from Group VB or an element with a coordination number of two from Group VIB, $R^x$ is selected from the group consisting of hydrogen, $C_1-C_{24}$ hydrocarbyl, $C_1-C_{24}$ hydrocarbyl substituted with one or more, typically one to twelve, halogen atoms, and $C_1-C_{24}$ alkoxy, and z is the coordination number of J. Preferred Q substituents are cyclopentadienyl, indenyl, fluorenyl, aminoboratobenzyl or $J(R^x)_{z-2}$ wherein J is nitrogen, phosphorus, oxygen or sulfur, and $R^x$ is $C_1-C_{12}$ alkyl optionally substituted with one or more, typically one to six, halogen atoms. Particularly preferred Q groups are $NR^x$ moieties wherein $R^x$ is lower alkyl or phenyl.

$Q^1$, $Q^2$, $Q^3$ and $Q^4$ are each a univalent radical, and are preferably independently selected from the group consisting of hydrido, halide, alkoxy, amido, and substituted or unsubstituted $C_1-C_{30}$ hydrocarbyl; if substituted, the substituents are typically although not necessarily electron-withdrawing groups such as a halogen atom, an alkoxy group, or the like, or the substituents may be Group IVB or Group VB elements. Alternatively, $Q^1$ and $Q^2$ and/or $Q^3$ and $Q^4$ may together form an alkylidene olefin (i.e., $=CR_2$ wherein R is hydrogen or hydrocarbyl, typically lower alkyl), acetylene, or a five- or six-membered cyclic hydrocarbyl group. Preferred $Q^1$, $Q^2$, $Q^3$ and $Q^4$ moieties are hydrido, amido, $C_1-C_{12}$ alkyl, and $C_1-C_{12}$ alkyl substituted with one or more halogen and/or alkoxy groups, typically one to six such groups, and $C_1-C_{12}$ alkyl substituted with a Group IVB element. Particularly preferred $Q^1$, $Q^2$, $Q^3$ and $Q^4$ moieties are hydrido, amido, lower alkyl and lower alkoxy.

$Q^5$ is an optional ligand having the structure of formula (I).

The subscripts k, l, m and n are independently zero or 1, preferably both m and n are zero, and letter "q" represents an optional double bond.

X is N, O, S or P, with the provisos that (a) when X is N or P, then either n is 1 or q is present as a double bond, but not both, and (b) when X is O or S, then n is zero and q is absent.

$R^1$, $R^6$ and $R^7$ are independently hydrido, hydrocarbyl or substituted hydrocarbyl, as defined above, and $R^2$ and $R^5$ are independently hydrido, halo, hydrocarbyl or substituted hydrocarbyl, or $R^1$ and $R^2$ and/or $R^5$ and $R^6$ may be taken together to form a linkage —Q*—, resulting in a five- or six-membered cyclic group. As explained above, Q* is —[(CR*)$_{a*}$(Z)$_{b*}$]— in which a* is 2, 3 or 4, Z is N, O or S, b* is zero, 1 or 2, the sum of a* and b* is 3 or 4, and R* is selected from the group consisting of hydrido, halo, hydrocarbyl, hydrocarbyloxy, trialkylsilyl, NR$^8_2$, OR$^9$, and NO$_2$, wherein R$^8$ or R$^9$ are each independently hydrocarbyl, or wherein R moieties on adjacent carbon atoms may be linked to form an additional five- or six-membered ring. R$^2$ and R$^5$ may together form a linkage —Q*— as just defined. Preferably, R$^6$ is a substituted or unsubstituted aromatic group, e.g., phenyl, 1-naphthyl, 2-naphthyl, 2-ethylphenyl, 2,6-diisopropylphenyl, 2,6-di-n-butylphenyl, 2,6-dimethylphenyl, 2-t-butylphenyl, 2,6-diphenylphenyl, 2,4,6-trimethylphenyl, 2-trifluoromethylphenyl, 4-bromo-2,6-dimethylphenyl, 3,5-dichloro-2,6-diethylphenyl, or 2,6-bis(2,6-dimethylphenyl)phenyl.

Examples of R$^1$, R$^6$ and R$^7$ thus include, but are not limited to, hydrido, methyl, ethyl, n-propyl, isopropyl, methoxy, ethoxy, isopropoxy, phenyl, benzyl, phenoxy, pyridyl, diisopropylphenyl, methoxyphenyl, trimethylsilyl, triethylsilyl, and the like; R$^2$ and R$^5$ substituents can include any of the foregoing as well as halogen substituents, i.e., chloro, fluoro, bromo and iodo, with chloro and fluoro preferred. When R$^1$ and R$^2$ and/or R$^5$ and R$^6$ are linked, the cyclic structures so formed may be alicyclic or aromatic, including, for example, furanyl, pyrrolyl, thiophenyl, imidazolyl, pyrazolyl, oxathiolyl, pyridinyl, methylpyridinyl, ethylpyridinyl, pyridazinyl, pyrimidinyl, pyrazinyl, piperidinyl, piperazinyl, morpholinyl, tetrahydrothiophenyl, tetrahydrofuranyl, tetrahydropyranyl, 1,4-dioxanyl, etc. When R$^2$ and R$^5$ are linked, the resulting structures are alicyclic and may or may not contain heteroatoms; such moieties include, for example, cyclopentane, cyclohexane, tetrahydrofuran, tetrahydropyran, tetrahydrothiophene, 1,4-dioxane, 1,2-dithiole, 1,3-dithiole, piperazine, morpholine, and the like.

R$^3$ and R$^4$ are independently selected from the group consisting of hydrido and hydrocarbyl, preferably hydrido or lower alkyl, or at least one of R$^3$ and R$^4$ may be bound through a lower alkylene linkage, preferably a methylene linkage, to an atom contained within L$^1$ or L$^2$.

M$^1$ is a transition metal, including, but not limited to, Mb, Ta, Mo, W, Mn, Re, V and Cr.

M$^2$ is a Group IIIA element, a Group IVA element, a Group VA element, a lanthanide, or an actinide. Particularly preferred M$^2$ moieties are Zr, Hf and Ti.

The letter "a" represents an integer of at least 1, "b" is zero, 1 or 2, and the sum of a and b is 2 or 3.

The complex may also contain additional BL$^1$ and/or BL$^2$ moieties.

One group of such compounds is represented by structural formula (V)

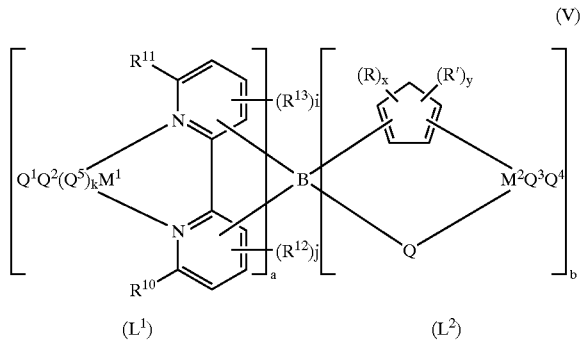

(V)

wherein:

a, b, B, M$^1$, M$^2$, R, R', k, x, y, Q, Q$^1$, Q$^2$, Q$^3$, Q$^4$ and Q$^5$ are as defined above with respect to formula (III);

R$^{10}$, R$^{11}$, R$^{12}$ and R$^{13}$ are independently hydrido, hydrocarbyl or substituted hydrocarbyl; and i and j are independently zero, 1, 2 or 3.

In another embodiment, complexes of the invention have the structure of formula (VI)

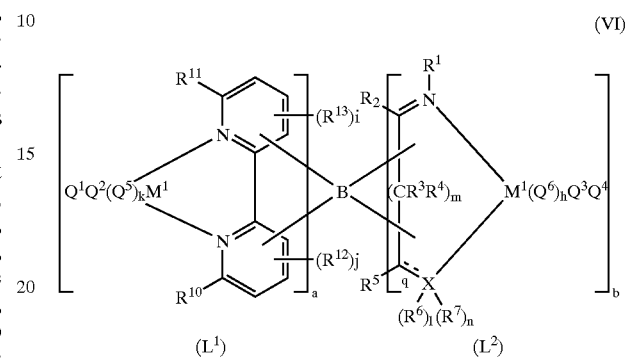

(VI)

wherein:

R$^1$, R$^2$, R$^3$, R$^4$, R$^5$, R$^6$, R$^7$, X, a, b, B, M$^1$, k, l, m, n, q, Q$^1$, Q$^2$, Q$^3$, Q$^4$ and Q$^5$ areas defined above with respect to formula (III);

Q$^6$ is an optional ligand having the structure of formula (I);

h is zero or 1;

R$^{10}$, R$^{11}$, R$^{12}$ and R$^{13}$ are independently hydrido, hydrocarbyl or substituted hydrocarbyl; and i and j are independently zero, 1, 2 or 3.

Another group of complexes is represented by structural formula (VII)

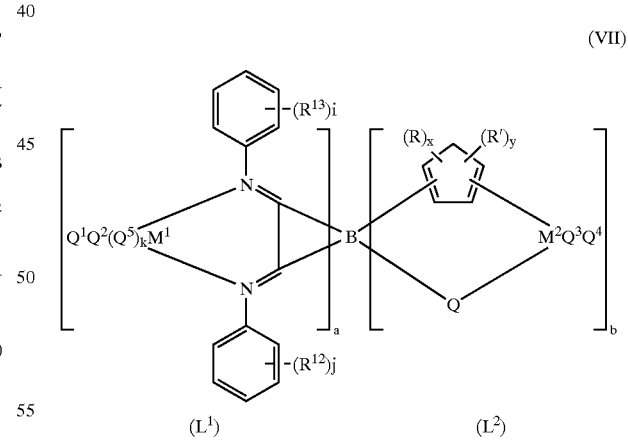

(VII)

wherein:

a, b, B, M$^1$, M$^2$, R, R', k, x, y, Q, Q$^1$, Q$^2$, Q$^3$, Q$^4$ and Q$^5$ are as defined above with respect to formula (III);

R$^{12}$ and R$^{13}$ are independently hydrido, hydrocarbyl or substituted hydrocarbyl; and i and j are independently zero, 1, 2 or 3.

In still another embodiment, complexes of the invention have the structure of formula (VIII)

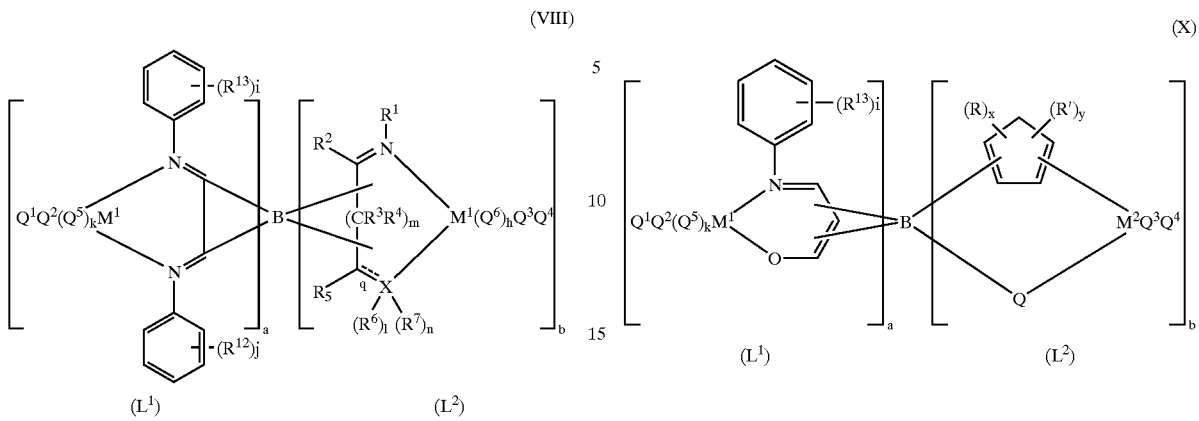

wherein:

$R^1$, $R^2$, $R^3$, $R^4$, $R^5$, $R^6$, $R^7$, X a, b, B, $M^1$, k, l, m, n, q, $Q^1$, $Q^2$, $Q^3$, $Q^4$ and $Q^5$ areas defined above with respect to formula (III);

$Q^6$ is an optional ligand having the structure of formula (I);

h is zero or 1;

$R^{12}$ and $R^{13}$ are independently hydrido, hydrocarbyl or substituted hydrocarbyl; and i and j are independently zero, 1, 2 or 3.

In still another embodiment, complexes of the invention have the structure of formula (IX)

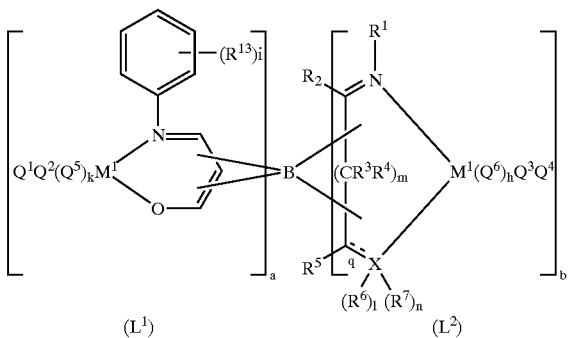

wherein:

$R^1$, $R^2$, $R^3$, $R^4$, $R^5$, $R^6$, $R^7$, X, a, b, B, $M^1$, k, l, m, n, q, $Q^1$, $Q^2$, $Q^3$, $Q^4$ and $Q^5$ are as defined above with respect to formula (III);

$Q^6$ is an optional ligand having the structure of formula (I);

h is zero or 1;

$R^{13}$ is independently hydrido, hydrocarbyl or substituted hydrocarbyl; and j is zero, 1, 2 or 3.

In yet another embodiment, complexes of the invention have the structure of formula (IX)

wherein:

a, b, B, $M^1$, $M^2$, R, R', k, x, y, Q, $Q^1$, $Q^2$, $Q^3$, $Q^4$ and $Q^5$ are as defined above with respect to formula (III);

$R^{13}$ is independently hydrido, hydrocarbyl or substituted hydrocarbyl; and j is zero, 1,2 or 3.

Specific catalysts encompassed by formulae (III), (V), (VI), (VII), (VIII), (IX) and (X) include, but are not limited to, the following:

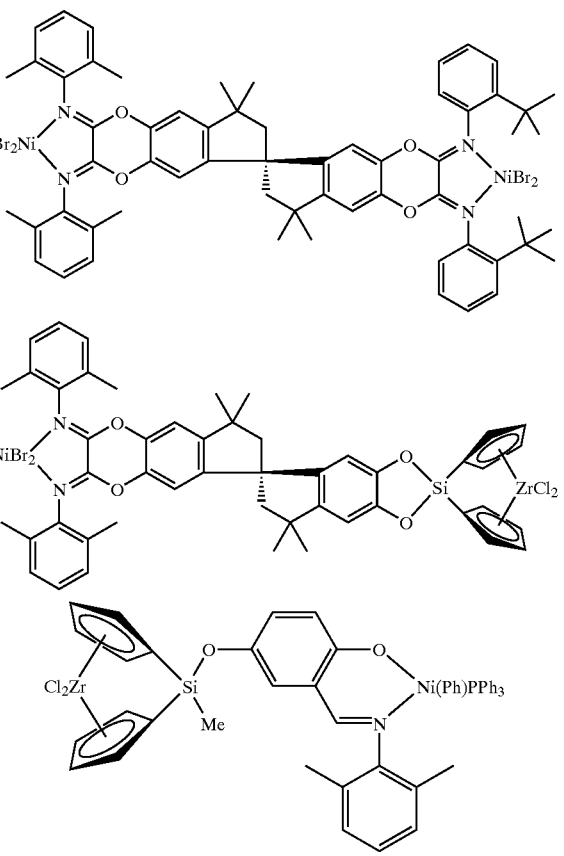

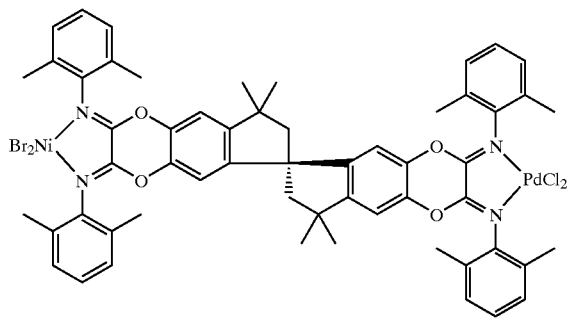
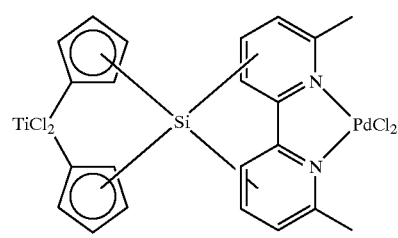
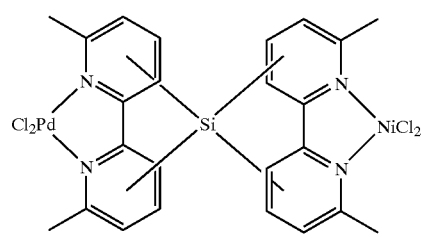
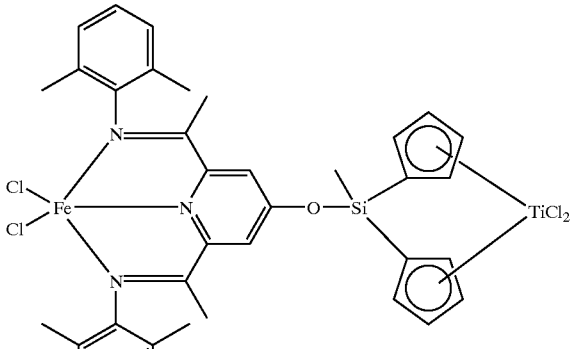
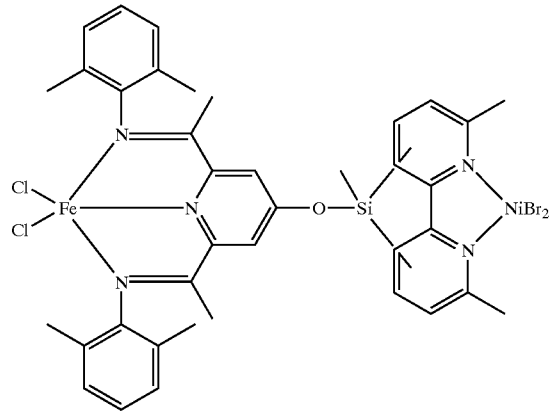
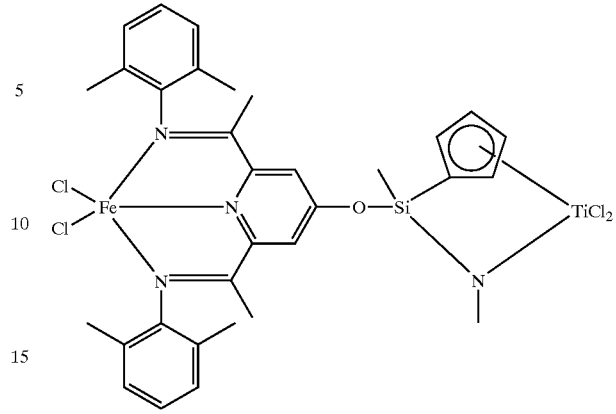
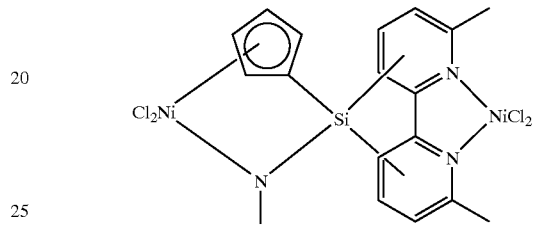
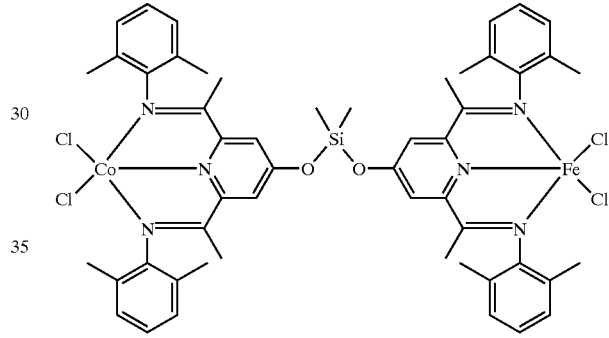

Synthesis

The complexes of the invention may be prepared using relatively simple and straightforward synthetic processes known to those skilled in the art and/or described in the pertinent texts and literature. For example, the complexes may be prepared by first providing an unsaturated nitrogenous ligand, $L^n$, which can be obtained commercially or chemically synthesized. See, e.g., PCT Publication Nos. WO 98/27124, WO 98/30612 and WO 98/49208, and U.S. Pat. No. 5,866,663, which describe such ligands and synthesis thereof. For example, an unsaturated nitrogenous ligand having the structural formula (XI)

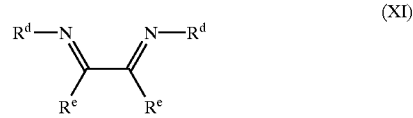

(XI)

wherein $R^d$ and $R^e$ are defined as any of $R^1$, $R^2$, $R^5$ and $R^6$, may be synthesized by addition of the primary amine $R^d$—$NH_2$ to the diketone of formula (XII)

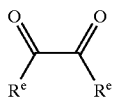

(XII)

in a simple, straightforward, one-step reaction.

Other unsaturated nitrogenous ligands may be synthesized in a similar manner, by reaction of a suitable primary amine with a selected aldehyde or a ketone. For example, the asymmetric ligand of formula (XIII)

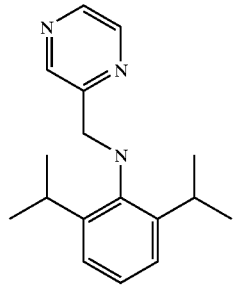

(XIII)

may be readily synthesized from 2,6-diisopropylaniline and 2-pyrazinecarboxaldehyde, as described, for example, in Weidenbruch et al. (1993) *Organometallic Chemistry* 454:35. Patai, *The Chemistry of the Carbon-Nitrogen Double Bond* (1970), also provides information on various synthetic methods that can be used in the preparation of unsaturated nitrogenous compounds.

The next step of the synthesis involves the use of a halogenated compound $B(Hal)_{2(a+b)}$ as a starting material (wherein B, a and b are as defined earlier herein and "Hal" represents a halogen atom). The compound is contacted with an alkali metal salt of the desired second ligand $L^x$, i.e., an unsaturated nitrogenous ligand or a cyclopentadienyl-based ligand to provide an intermediate $L^n{}_aB(Hal)_b$. Next, the intermediate is successively reacted with an alkali metal salt of $L^n$, thus providing the intermediate $L^n{}_aBL^x{}_b$. This intermediate is deprotonated and metallated as described below.

In an alternative method, a starting material $B(Hal)_4$ is caused to react with an alkali metal salt of the $L^n$ ligand. The product is then contacted with an alkali metal salt of an aromatic compound Ar, containing one to three cyclopentadienyl rings, either substituted or unsubstituted, to provide an intermediate $L^nBAr_2$. (When it is desired that the end product contain different aromatic groups, successive reaction with different aromatic salts is carried out, i.e., $L^nB$ (Hal)$_2$ is first reacted with an alkali metal salt of a first aromatic species $Ar_1$, then with an alkali metal salt of a second aromatic species $Ar_2$, and the like.) This intermediate is then used to prepare the compound $L^n{}_aLB^x{}_b$. Metallation is then carried out using metal complexes generally of the form $MQ'Q'Y_2$ wherein M is a transition metal Q' is $Q^1$, $Q^2$, $Q^3$ or $Q^4$ as defined earlier herein, and the Y substituents are leaving groups that are typically halide, pseudohalide (e.g., lower alkoxy such as methoxy), flurohydrocarbylborate, etc. During the metallation reaction, the Y groups are eliminated.

Oxamides may also be used as starting materials. In this method, a oxallyl chloride is reacted with two equivalents of a primary amine in the presence of THF. If desired, equal molar equivalents of different primary amines may be sequentially added. Once the oxamide has been synthesized, it is reacted with $PCl_5$ or $POCl_3$ or the like to form a bis-imidoylchloride. The bis-imidoylchloride ligand may then be reacted with a diol bridging compound in the presence of triethylamine, a two molar equivalent of sodium hydride, and THF to form a bridged ligand complex. This complex may then be metallated as discussed above. Other suitable metallation reactions for preparing the present complexes will be known to those skilled in the art and/or described in or readily derived from the pertinent texts and literature.

Preparation of the Catalyst System

The novel compounds of the invention, when used as polymerization catalysts, are used in conjunction with a conventional catalyst activator as will be appreciated by those skilled in the art. Thus, prior to use, the compounds of the invention are incorporated into a catalyst system that includes such an activator. Suitable catalyst activators include, but are not limited to, metal alkyls, hydrides, alkylhydrides, and alkylhalides, such as alkyllithium compounds, dialkylzinc compounds, trialkyl boron compounds, trialkylaluminum compounds, alkylaluminum halides and hydrides, and tetraalkylgermanium compounds. Specific examples of useful activators include n-butyllithium, diethylzinc, di-n-propylzinc, triethylboron, triethylaluminum, triisobutylaluminum, tri-n-hexylaluminum, ethylaluminum dichloride, dibromide and dihydride, isobutyl aluminum dichloride, dibromide and dihydride, di-n-propylaluminum chloride, bromide and hydride, diisobutyl-aluminum chloride, bromide and hydride, ethylaluminum sesquichloride, methyl aluminoxane ("MAO"), hexaisobutyl aluminoxane, tetraisobutyl aluminoxane, polymethyl aluminoxane, tri-n-octylaluminum, tetramethyl germanium, and the like. Other activators that are typically referred to as ionic cocatalysts may also be used; such compounds include, for example, $(C_6H_6)_3{}^+$, $C_6H_5$—$NH_2CH_3{}^+$, and fluorohydrocarbylboron compounds such as tetra(pentafluorophenyl)borate, sodium tetrakis[(bis-3,5-trifluoromethyl)phenyl]borate, $H^+(OCH_2CH_3)_2$[(bis-3,5-trifluoromethyl)-phenyl]borate, trityltetra(pentafluorophenyl)borate and tris (pentafluorophenyl)boron. Mixtures of activators may, if desired, be used. Generally, the catalyst activator is such that upon combination with a compound of the invention, a catalytically active ionic species results.

For liquid phase or slurry polymerization, the catalyst and activator are generally mixed in the presence of inert diluents such as, for example, aliphatic or aromatic hydrocarbons, e.g., liquified ethane, propane, butane, isobutane, n-butane, n-hexane, isooctane, cyclohexane, methylcyclohexane, cyclopentane, methylcyclopentane, cycloheptane, methylcycloheptane, benzene, ethylbenzene, toluene, xylene, kerosene, Isopar® M, Isopar® E, and mixtures thereof. Liquid olefins, or the like, which serve as the monomers or comonomers in the polymerization process may also serve as the diluent; such olefins include, for example, ethylene, propylene, butene, 1-hexene and the like. The amount of catalyst in the diluent will generally be in the range of about 0.01 to 1.0 mmoles/liter, with activator added such that the ratio of catalyst to activator is in the range of from about 10:1 to 1:2000, preferably in the range of from about 1:1 to about 1:200, on a molar basis.

Preparation of the catalyst/activator/diluent mixture is normally carried out under anhydrous conditions in the absence of oxygen, at temperatures in the range of from about −90° C. to about 300° C., preferably in the range of from about −10° C. to about 200° C.

The catalyst, activator and diluent are added to a suitable reaction vessel, in any order, although, as noted above, the catalyst and activator are usually mixed in the diluent and the mixture thus prepared then added to the reactor.

A further embodiment of the invention provides a method of synthesizing arrays of metal-ligand compounds using the multimodal catalysts of the invention. In the method at least two different metal-binding amino alcohol-derived ligands are synthesized on or delivered to a substrate. These ligands may be supported or unsupported prior to contact with the substrate. Once in contact with the substrate, the ligands are metallated, as described above, forming metal-ligand compounds. Each of the ligands may be metallated with the same or different Group IV A, Group VA or Group VIA metals.

Preparation of Catalyst Arrays

In a still further embodiment, methods are provided for synthesizing and screening arrays of multimodal metal-ligand compounds. In the method at least two alkali metal salts of different $L^n$ metal-binding, unsaturated nitrogenous ligands are synthesized on or delivered to a substrate. These ligands may be supported or unsupported prior to contact with the substrate. Once in contact with the substrate, the ligands are contacted with a halogenated compound $B(Hal)_{2(a+b)}$ (wherein B, a and b are as defined earlier herein and "Hal" represents a halogen atom) to provide intermediate $L^n{}_a B(Hal)_b$ compounds Next, the intermediates are successively reacted with alkali metal salts of the desired second ligands $L^x$, i.e., unsaturated nitrogenous ligands or a cyclopentadienyl-based ligands, thus providing intermediate $L^n{}_a BL^x{}_b$ compounds. These intermediates are deprotonated and metallated as described above. Each of the ligands may be metallated with the same or different Group IV A, Group VA or Group VIA metals. The multimodal metal-ligand compounds may be activated using one or more conventional catalyst activators.

In a still further embodiment, methods are provided for forming and screening arrays of multimodal metal-ligand compounds of the invention. In the method at least two different multimodal metal-ligand compounds are synthesized on a substrate. Again, these ligands may be supported or unsupported prior to contact with the substrate. The multimodal metal-ligand compounds may be synthesized in an array or may be placed in an array arrangement after synthesis. The multimodal metal-ligand compounds may be screened for purity and identity using conventional. Typical screening and characterizing techniques such as mass spectrometry, calorimetry, digital autoradiography, polarimetry, imaging polarimetry, infrared spectroscopy, reflectance spectroscopy, uv-vis spectroscopy, chemisorption, surface area (BET) measurements, uv-vis fluorescence, phosphorescence, chemiluminescence, Raman spectroscopy, NIR spectroscopy, magnetic resonance imaging, NMR spectroscopy, Electron Spin Resonance (ESR) spectroscopy, gas chromatography, high performance liquid chromatography (HPLC), x-ray diffraction, neutron diffraction, refractometry, circular dichroism, electron spectroscopy, scanning electron microscopy (SEM), transmission electron microscopy (TEM), scanning tunneling microscopy (STM), and the like.

The multimodal metal-ligand compounds may then be used in catalyzing reactions. During and after the catalyzed reactions, the multimodal metal-ligand compounds and the resulting products can be screened for useful properties using conventional screening and characterizing techniques such as chemical or biological testing; mass spectrometry; reaction calorimetry; parallel reaction calorimetry; parallel differential scanning calorimetry; viscosity measurement; digital autoradiography; thermal imaging; polarimetry; imaging polarimetry; infrared spectroscopy; IR imaging; reflectance spectroscopy; uv-vis spectroscopy; chemisorption; surface area (BET) measurements; uv-vis fluorescence; phosphorescence; chemiluminescence; Raman spectroscopy; NIR spectroscopy; magnetic resonance imaging; NMR spectroscopy; gas chromatography; high performance liquid chromatography (HPLC); gel permeation chromatography (GPC); TREF; x-ray diffraction; neutron diffraction; refractometry; circular dichroism; turbidimetry; electron spectroscopy; scanning electron microscopy (SEM); transmitting electron microscopy (TEM); scanning tunneling microscopy (STM).

The array of products can also be used to screen for important chemical and physical properties such as solvent extractables, solubility, porosity, weatherability, uv-vis stability, scratch resistance, abrasion resistance, wettability, hardness, color, dielectric constant, moisture absorption, solvent swelling, gloss, adhesion, heat aging, shear, stain resistance, and scrub resistance. Screening may be performed either simultaneously, serially and/or in a spatially selective manner, i.e., wherein the detector used is distanced from the array, the array is screened and the detector is then repositioned so that a different portion of the array is screened.

Use in Polymerization

The novel catalysts are used to prepare polymeric compositions using conventional polymerization techniques known to those skilled in the art and/or described in the pertinent literature. The monomer(s), catalyst and catalyst activator are contacted at a suitable temperature at reduced, elevated or atmospheric pressure, under an inert atmosphere, for a time effective to produce the desired polymer composition. The catalyst may be used as is or supported on a suitable support. In one embodiment, the novel catalysts are used as homogeneous catalysts, i.e., as unsupported catalysts, in a gas phase or liquid phase polymerization process. A solvent may, if desired, be employed. The reaction may be conducted under solution or slurry conditions, in a suspension using a perfluorinated hydrocarbon or similar liquid, in the gas phase, or in a solid phase powder polymerization.

Liquid phase polymerization generally involves contacting the monomer or monomers with the catalyst/activator mixture in the polymerization diluent, and allowing reaction to occur under polymerization conditions, i.e., for a time and at a temperature sufficient to produce the desired polymer product. Polymerization may be conducted under an inert atmosphere such as nitrogen, argon, or the like, or may be conducted under vacuum. Preferably, polymerization is conducted in an atmosphere wherein the partial pressure of reacting monomer is maximized. Liquid phase polymerization may be carried out at reduced, elevated or atmospheric pressures. In the absence of added solvent, i.e., when the olefinic monomer serves as the diluent, elevated pressures are preferred. Typically, high pressure polymerization in the absence of solvent is carried out at temperatures in the range of about 0° C. to about 300° C., preferably in the range of about 50° C. to about 200° C., and at pressures on the order of 1 to 5,000 atm, typically in the range of about 10 to 500 atm. When solvent is added, polymerization is generally conducted at temperatures in the range of about 0° C. to about 200° C., preferably in the range of about 50° C. to about 100° C., and at pressures on the order of 10 to 500 atm.

Polymerization may also take place in the gas phase, e.g., in a fluidized or stirred bed reactor, using temperatures in the range of approximately 60° C. to 120° C. and pressures in the range of approximately 10 to 1000 atm.

The monomer or comonomers used are addition polymerizable monomers containing one or more degrees of unsaturation. Olefinic or vinyl monomers are preferred, and particularly preferred monomers are a-olefins having from about 2 to about 20 carbon atoms, such as, for example, linear or branched olefins including ethylene, propylene, 1-butene, 3-methyl-1-butene, 1,3-butadiene, 1-pentene, 4-methyl-1-pentene, 1-hexene, 4-methyl-1-hexene, 1,4-hexadiene, 1,5-hexadiene, 1-octene, 1,6-octadiene, 1-nonene, 1-decene, 1,4-dodecadiene, 1-hexadecene, 1-octadecene, and mixtures thereof. Cyclic olefins and diolefins may also be used; such compounds include, for example, cyclopentene, 3-vinylcyclohexene, norbornene, 5-vinyl-2-norbornene, 5-ethylidene-2-norbornene, dicyclopentadiene, 4-vinylbenzocyclobutane, tetracyclododecene, dimethano-octahydronaphthalene, and 7-octenyl-9-borabicyclo-(3,3,1)nonane. Aromatic monomers that may be polymerized using the novel metallocenes include styrene, o-methyl styrene, m-methyl styrene, p-methyl styrene, p-tert-butylstyrene, m-chlorostyrene, p-chlorostyrene, p-fluorostyrene, indene, 4-vinylbiphenyl, acenaphthalene, vinylfluorene, vinylanthracene, vinylphenanthrene, vinylpyrene and vinylchrisene. Other monomers that may be polymerized using the present catalysts include methylmethacrylate, ethylacrylate, vinyl silane, phenyl silane, trimethylallyl silane, acrylonitrile, maleimide, vinyl chloride, vinylidene chloride, tetrafluoroethylene, isobutylene, carbon monoxide, acrylic acid, 2-ethylhexylacrylate, methacrylonitrile and methacrylic acid.

In gas and slurry phase polymerizations, the catalyst is used in a heterogeneous process, i.e., supported on an inert inorganic substrate. Conventional materials can be used for the support, and are typically particulate, porous materials; examples include oxides of silicon and aluminum, or halides of magnesium and aluminum. Particularly preferred supports from a commercial standpoint are silicon dioxide and magnesium dichloride.

The polymeric product resulting from the aforementioned reaction may be recovered by filtration or other suitable techniques. If desired, additives and adjuvants may be incorporated into the polymer composition prior to, during, or following polymerization; such compounds include, for example, pigments, antioxidants, lubricants and plasticizers.

As explained earlier herein, the invention enables preparation of polymer compositions that are multimodal in nature, typically, but not necessarily, having a multimodal molecular weight distribution. That is, the catalysts used herein contain two or more active sites at which propagation rates differ, or that have different temperature sensitivities and/or $H_2$ responsiveness or the like. In this way, the type and degree of multimodality in the polymeric product can be controlled as desired. Multimodal polymer compositions are useful insofar as rheological behavior, mechanical strength and elasticity can be improved relative to corresponding compositions that are not multimodal.

The compounds of the invention are also useful in catalyzing other types of reactions, i.e., reactions other than polymerizations. Such reactions include, but are not limited to, hydrogenation, dehydrocoupling, cyclization, substitution, carbomagnesation and hydrosilylation. Methods for using the metal complexes of the invention to catalyze the aforementioned reactions and others will be known to those skilled in the art and/or described in the pertinent texts and literature.

EXPERIMENTAL

It is to be understood that while the invention has been described in conjunction with the preferred specific embodiments thereof, that the foregoing description is intended to illustrate and not limit the scope of the invention. Other aspects, advantages and modifications within the scope of the invention will be apparent to those skilled in the art to which the invention pertains.

All patents, patent applications, and publications mentioned herein are hereby incorporated by reference in their entireties.

EXAMPLE 1

Synthesis of Multinuclear Compound

This example describes synthesis of a multinuclear compound of the invention, with synthesis of a imine-containing ligand described in part (a), binding of the ligand to the covalent bridging group described in part (b), metallation of the first imine-containing ligand described in part (c) and metallation of the remaining ligand described in part (d).

(a) Synthesis of the imine-containing ligand: The imine-containing ligand 1 may be synthesized as illustrated in Schemes 1 and 2. First, diketone a is reacted with 2 equimolar amounts of b, 2,6-dimethylphenylamine, in THF to form diamide 1, N,N'-bis(2,6-dimethylphenyl) ethane-1,2-diamide.

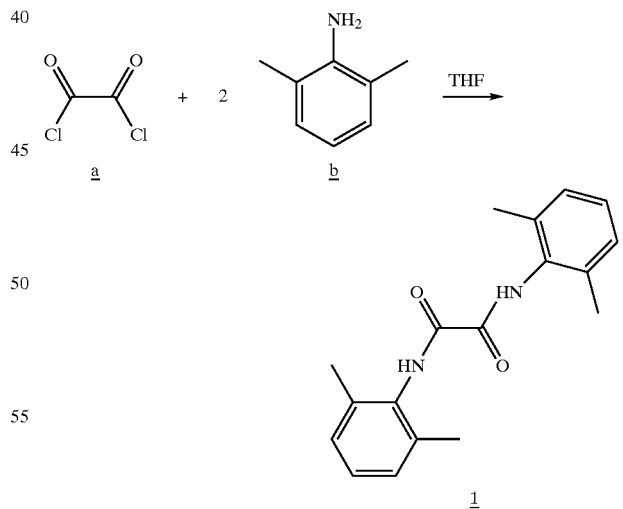

SCHEME 1

Second, as shown is Scheme 2, an approximately 2:1 molar ratio mixture of $PCl_5$ to oxamide 1, is stirred at reflux at 110° C. in toluene for 3 hours. Crystallization of the crude reaction mixture from cold pentane yields the desired ligand 2 1,4-diaza-1,4-bis(2,6-dimethylphenyl)-2,3-dichlorobuta-1,3-butadiene

SCHEME 2

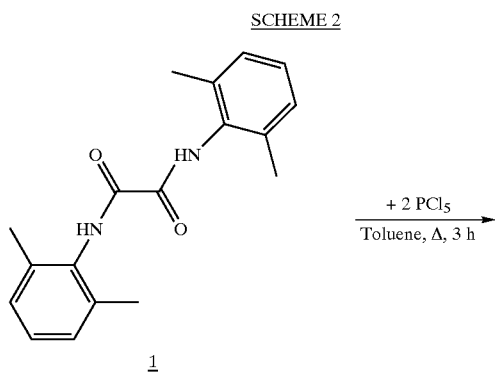

(b) Binding of the ligand to the covalent bridging group: As depicted in Scheme 3, an approximately 2:4:1 molar ratio mixture of ligand 2 to NaH, to bridging group 3, 3,3,3',3'-tetramethyl-1,1'-spirobisindane-5,5',6,6'-tetrol (Aldrich Chemical), is stirred at 80° C. in NEt₃ and THF for 3 hours to form the bridged ligand compound 4.

SCHEME 3

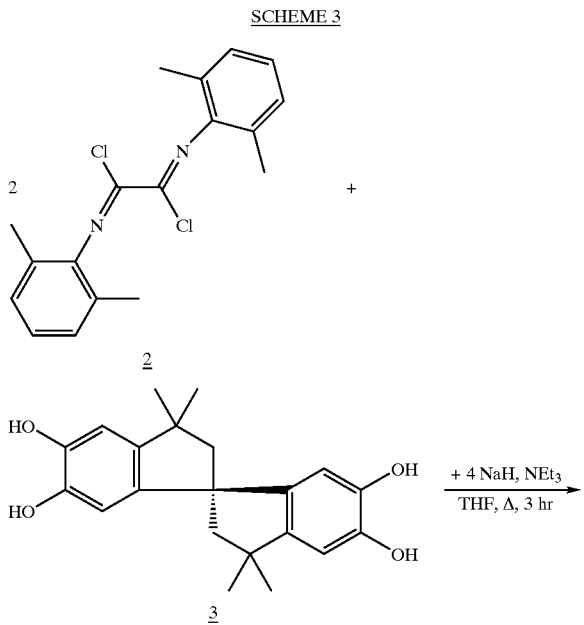

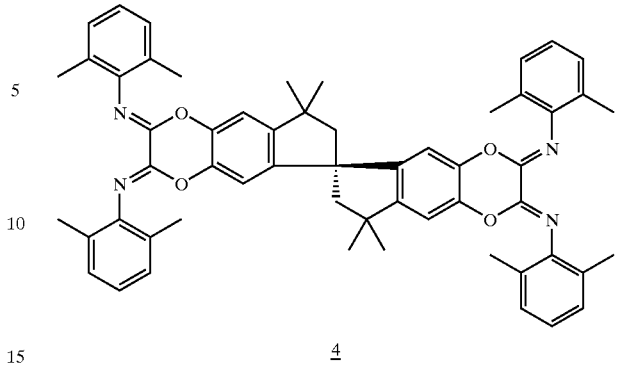

(c) Metallation of the imine-containing ligand: One of the imine-containing ligands in the bridged compound is then metallated by reacting the compound 4 with an equal molar amount of ((DME)NiBr₂ in diethyl ether to form semi-metallated compound 5 as illustrated below in Scheme 4.

SCHEME 4

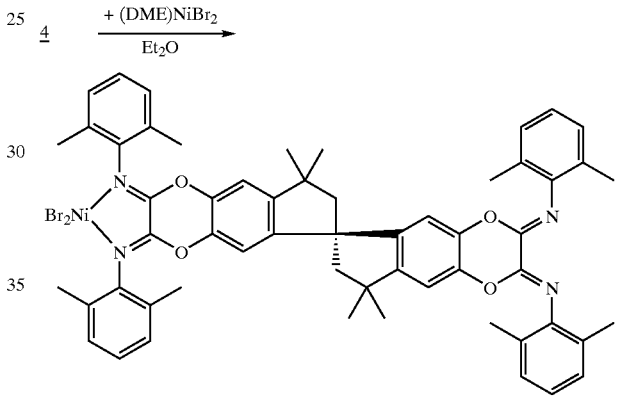

(e) Metallation of the remaining ligand: The remaining ligand in the bridged compound is then metallated by reacting the compound 5 with an equal molar amount of (COD)PdCl₂ slurried in diethylether to form multinuclear compound 6 as illustrated in Scheme 5.

SCHEME 5

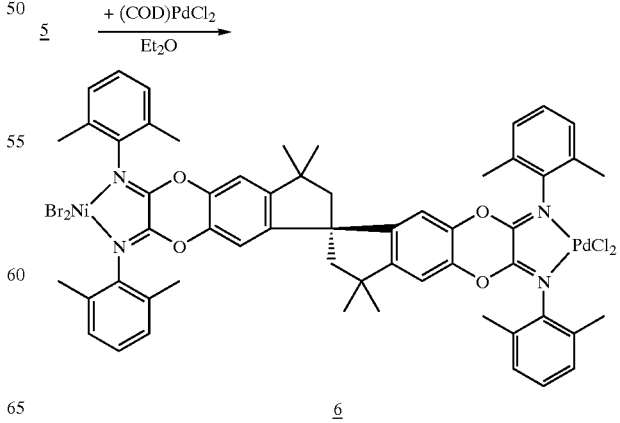

The mixture is then filtered and the solvent removed. The solid is washed with pentane and multinuclear compound 6 collected.

EXAMPLE 2

Synthesis of Multinuclear Compound

This example describes an alternative synthesis of a multinuclear compound of the invention. Synthesis of a first imine-containing ligand as described in Example 1. Formation of a second imine-containing ligand is described in part (a), binding of the first ligand to the bridging group is described in part (b), binding of the second ligand to the bridging group is described in part (c) and metallation of both ligands is described in part (d).

(a) Formation of a second imine-containing ligand: A second imine-containing ligand 8 may be synthesized as illustrated in Schemes 6 and 7. First, oxallyl chloride a is reacted with 2 equivalents of 2-t-butylaniline c, in THF to form diamide 7 N,N'-bis-(2-t-butylphenyl)ethane diamide.

SCHEME 6

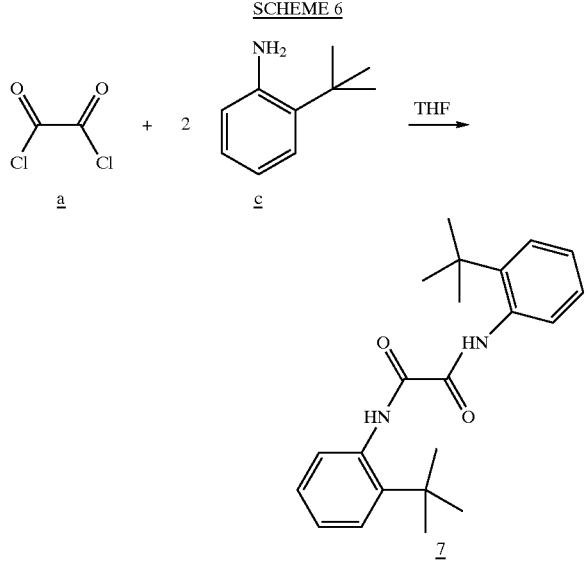

Second, as shown is Scheme 7, an approximately 2:1 molar ratio mixture of PCl₅ to diamide 7, is stirred at reflux at 110° C. in toluene for 3 hours. Crystallization of the crude reaction mixture from cold pentane yields the desired ligand 8

SCHEME 7

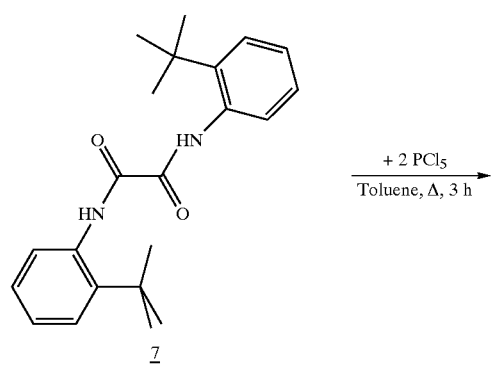

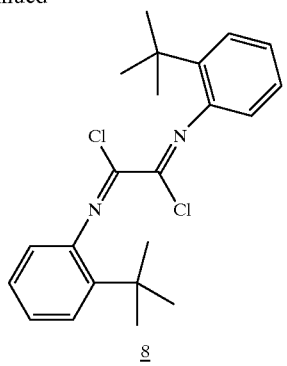

8

(b) Binding of the first ligand to the covalent bridging group: As depicted in Scheme 8, an approximately 1:2:1 molar ratio mixture of ligand 2, as prepared in Example 1, to NaH, to bridging group 3, is stirred at reflux at 80° C. in NEt₃ and THF for 3 hours to form the semi-bridged ligand compound 9.

SCHEME 8

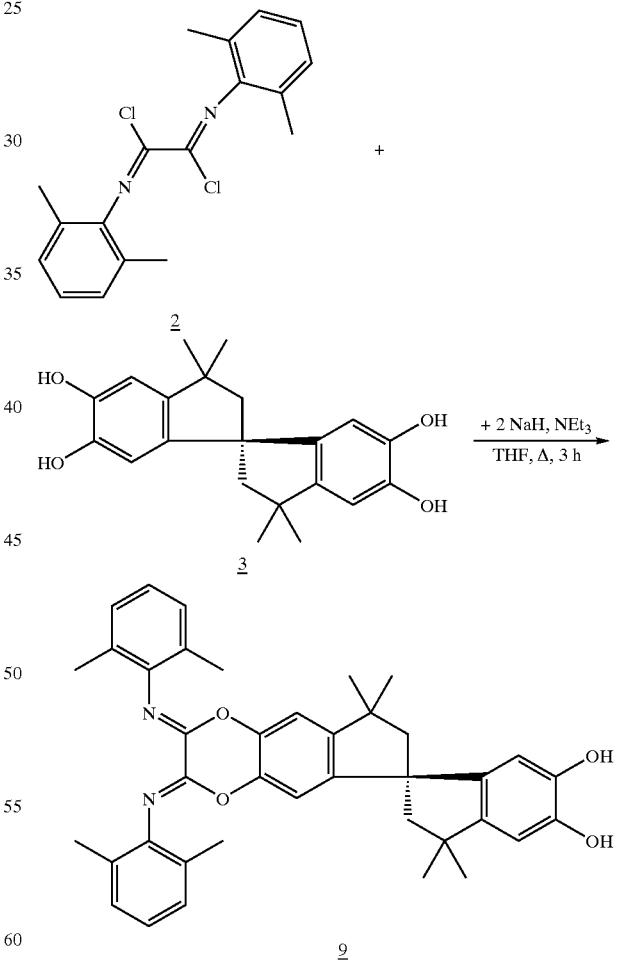

(c) Binding of the second ligand to the semi-bridged ligand compound: As epicted in Scheme 9, an approximately 1:2:1 molar ratio mixture of ligand 8, to NaH, to semi-bridged ligand compound 9, is stirred at reflux in NEt₃ and THF for 3 hours to form the bridged ligand compound 10.

SCHEME 9

9 + 8 →(+ 2 NaH, NEt₃ / THF, Reflux, 3h)

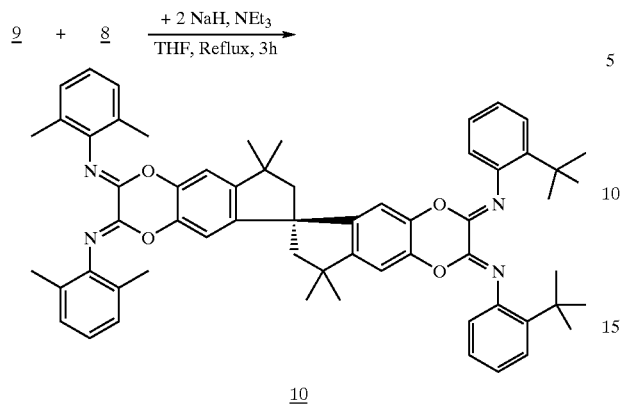

10

(d) Metallation of the bridged ligand compound: Both of the imine-containing ligands in the bridged compound are then metallated by reacting the compound 10 with a 2:1 molar amount of ((DME)NiBr₂ in diethylether to form multinuclear compound 11 as illustrated below in Scheme 10.

SCHEME 10

10 →(+ 2 (DME)NiBr₂ / Et₂O)

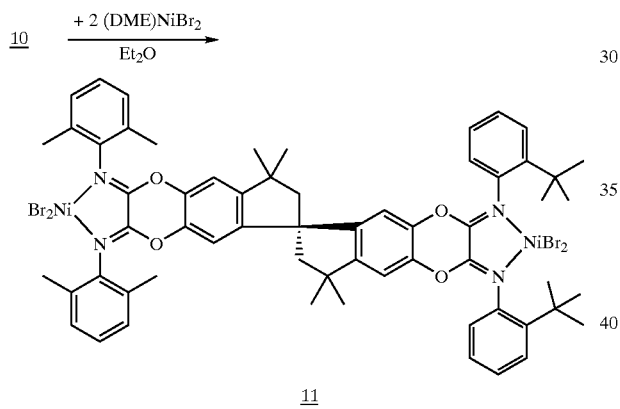

11

The mixture is then filtered and the solvent removed. The solid is washed with pentane and multinuclear compound 11 collected.

EXAMPLE 3

Synthesis of Multinuclear Compound

This example describes an alternative synthesis of a multinuclear compound of the invention. Synthesis of a imine-containing ligand and binding of the ligand to the bridging group is as described in Examples 1 and 2. Binding of a silicon-containing ligand to the semi-bridged ligand compound is described in part (a), metallation the silicon-containing ligand is described in part (b) and metallation of the imine-containing ligand is described in part (c).

(a) Binding of a silicon-containing ligand to the semi-bridged ligand compound: The semi-bridged ligand compound 9, is synthesized using the methods described in Examples 1 and 2. As depicted in Scheme 11, an approximately 1:2:1 molar ratio mixture of ligand 12, to NEt₃, to semi-bridged ligand compound 9, is stirred at room temperature in THF to form the bridged ligand compound 13.

SCHEME 11

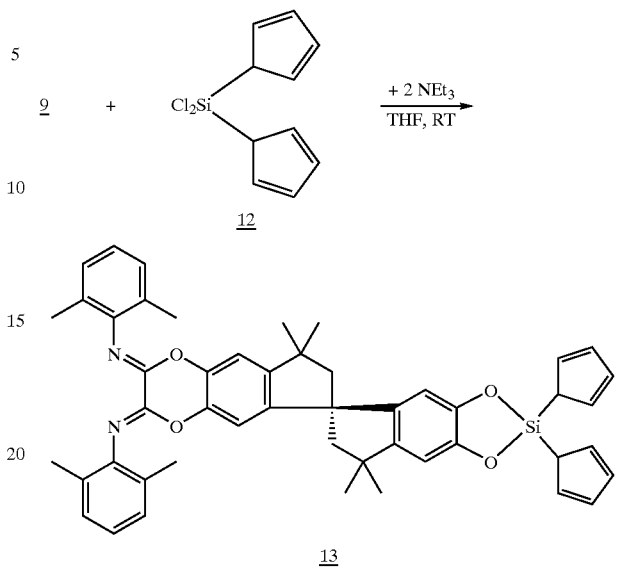

13

(b) Metallation of the bridged ligand compound: The Si-containing ligands in the bridged compound is then metallated by reacting the compound 13 with an approximately 1:2:1 molar ratio mixture of bridged ligand 13, to BuLi, to ZrCl₄, in diethylether to form semi-metallated compound 14 as illustrated below in Scheme 12.

SCHEME 12

13 + →(1) 2 BuLi / 2) ZrCl₄ / Et₂O)

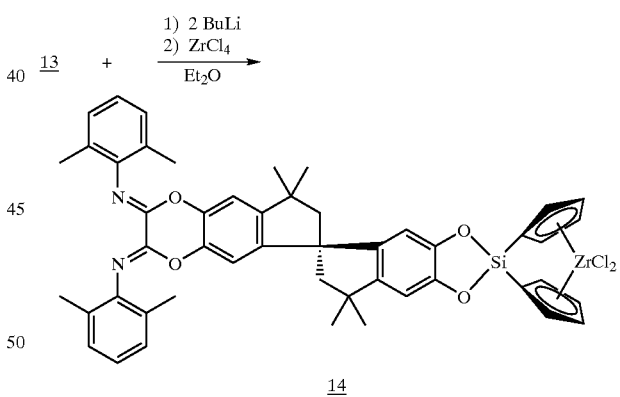

14

(c) Metallation of the imine-containing ligand: The imine-containing ligand in the bridged compound is then metallated by reacting the compound 14 with an equal molar amount of (COD)PdCl₂ slurried in diethyl ether to form multinuclear compound 15 as illustrated in Scheme 13.

SCHEME 13

14 →(+ (COD)PdCl₂ / Et₂O)

-continued

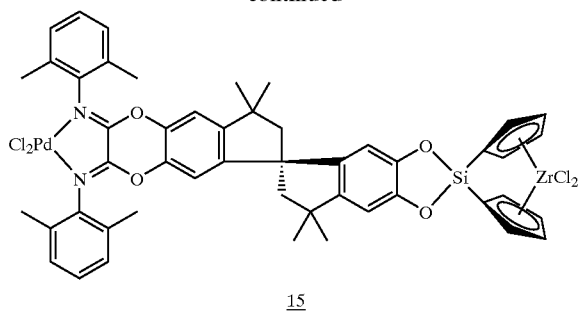

15

The mixture is then filtered, the solvent removed and multinuclear compound 15 collected.

EXAMPLE 4

Synthesis of Multinuclear Compound

This example describes synthesis of a multinuclear compound of the invention, with synthesis of a salicylaldimine ligand and bridging compound described in part (a), metallation of the salicylaldimine ligand and bridging compound described in part (b), binding of the metallated ligand and bridging group to a silicon-containing ligand described in part(c) and metallation of the silicon-containing ligand described in part (d).

(a) Synthesis of the salicylaldimine ligand and bridging compound: The salicylaldimine ligand and bridging compound 16 was synthesized as illustrated in Scheme 14. 2,5-Dihydroxybenzaldehyde (0.644 g) c was mixed with an equimolar amount of 2,6-dimethylaniline, b, in methanol and stirred for 16 hours at room temperature. The solution was then evaporated to dryness and extracted with dichloromethane. Hexane was then added, causing a black precipitate to form. The mixture was filtered to give a red gel. 'HNMR indicted that the red gel was salicylaldimine ligand 16, 2.20 (s, 6H), 6.82 (s, 1H), 6.96 (s, 2H), 7.03 (m, 1H), 7.10 (m, 2H), 8.23 (s, 1H).

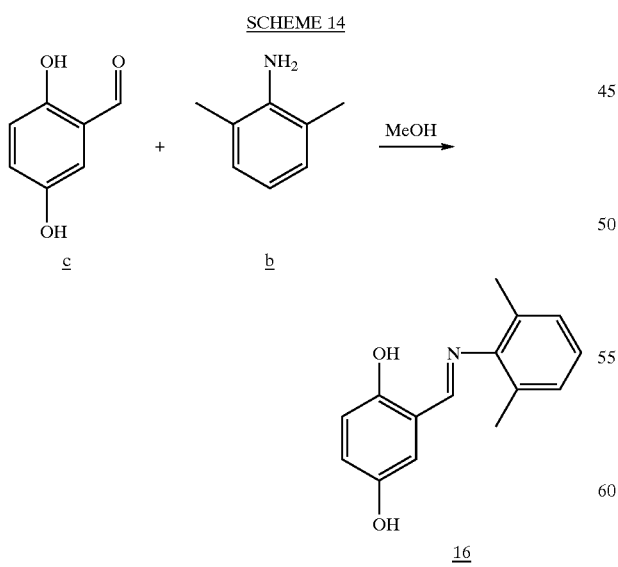

SCHEME 14

(b) Metallation of the salicylaldimine ligand and bridging compound: The salicylaldimine ligand in the salicylaldimine ligand and bridging compound is then metallated by reacting the compound 16 with an approximately 1:1:1 molar ratio mixture of compound 16, to NaH, to trans-$(PPh_3)_2Ni(Ph)Cl$, in THF to form metallated compound 17 as illustrated below in Scheme 15.

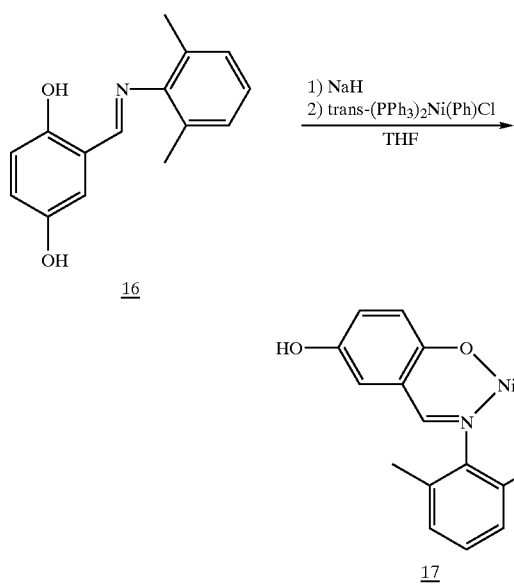

SCHEME 15

(c) Binding of a silicon-containing ligand to the metallated compound: As depicted in Scheme 16, an approximately 1:1:1 molar ratio mixture of ligand 12, to $NEt_3$, to semi-metallated compound 17, is stirred at room temperature in diethyl ether to form the semi-metallated bridged compound 18,

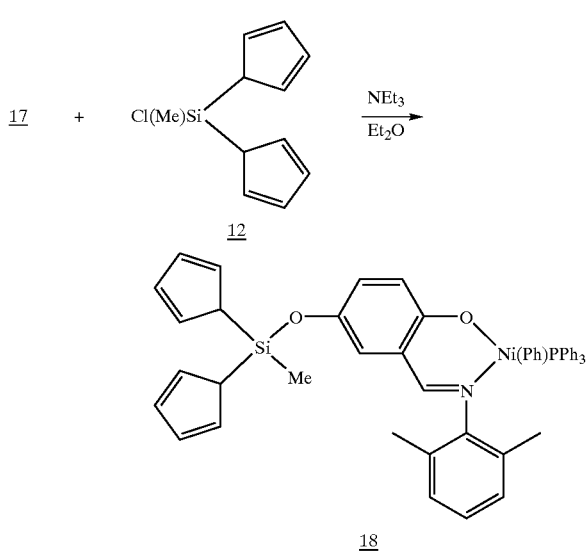

SCHEME 16

(d) Metallation of the semi-metallated bridged compound: The imine-containing ligands in the semi-metallated bridged compound is then metallated by reacting the compound 18 with an equal molar amount of $Zr(NMe_2)_4$ in diethyl ether to form multinuclear compound 19 as illustrated below in Scheme 17.

SCHEME 17

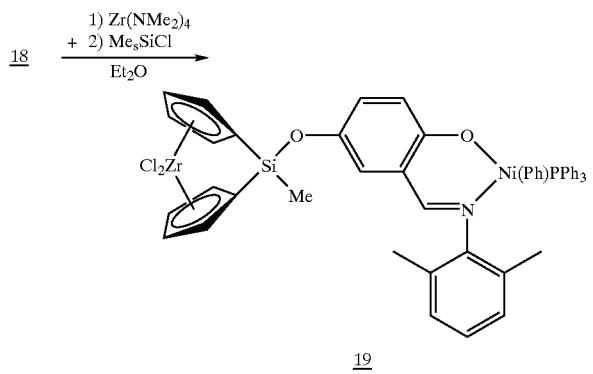

EXAMPLE 5

Preparation of Bimodal Polyethylene

The metallocene compounds prepared in Example 2 is used as polymerization catalysts in the preparation of polyethylene ("PE") having a bimodal branching distribution. Standard ethylene polymerization conditions are used, as follows: Polymerizations are conducted in a 300 mL autoclave reactor. Methyl aluminoxane (MAO) is used as co-catalyst with total Al/M ratio equal to 300. Prior to initiation of polymerization, the reactors are loaded with 160 mL of toluene and the MAO. The reactors are heated to the desired reaction temperature and pressurized with ethylene to 100 psig. The reactors are configured to maintain the set pressure and temperature during the polymerization reaction. The reaction is initiated by injection of the catalyst. The reactions are run for 30 minutes and terminated by injection of acidified methanol (2% HCl). The polymer is removed from the reactor and washed with additional acidified methanol, aqueous $NaHCO_3$, water and acetone. The resulting polymer is dried in a vacuum oven overnight and displays a bimodal molecular weight distribution.

What is claimed is:

1. A catalyst system comprising an organometallic complex having the structure of formula (III)

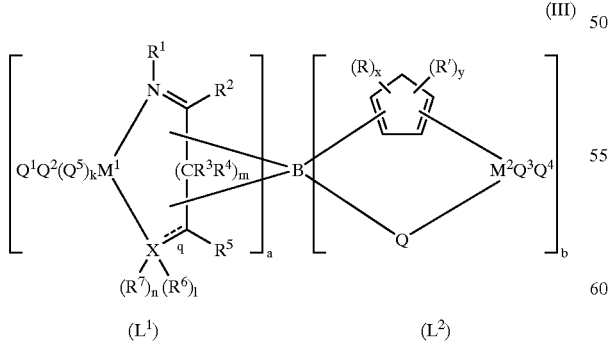

wherein:

B is a covalent bridging group comprising carbyl, silyl, disilyl, germanyl, ammonium, phosphonium,

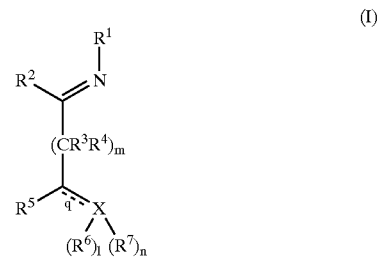

or a $C_1-C_{30}$ hydrocarbylene, substituted hydrocarbylene, heterohydrocarbylene, or substituted heterohydrocarbylene radical, optionally containing a Group IVB element, a Group VB element, or both a Group IVB element and a Group VB element, and is capable of binding up to $n_{max}$ substituents through single covalent bonds, wherein $n_{max}$ is at least 4;

R and R' are independently selected from the group consisting of halogen, $C_1-C_{24}$ hydrocarbyl, $C_1-C_{24}$ hydrocarbyl substituted with one or more halogen atoms, and $C_1-C_{24}$ hydrocarbyl-substituted Group IVB elements;

x is 0, 1, 2, 3, or 4, and y is 0, 1, 2, 3, or 4, with the proviso that the sum of x and y cannot exceed 4, or, when R and R' are ortho to each other and x and y are each 1 or greater, R and R' can together form a five- or six-membered cyclic structure optionally substituted with one to four substituents selected from the group consisting of halogen, $C_1-C_{24}$ hydrocarbyl, $C_1-C_{24}$ hydrocarbyl substituted with one or more halogen atoms, and $C_1-C_{24}$ hydrocarbyl-substituted Group IVB elements, q is an optional double bond, and X is N, O, S, or P, with the provisos that (a) when X is N or P, then either n is 1 or q is present as a double bond, but not both, and (b) when X is O or S, then n is zero and q is absent;

$R^1$, $R^6$, and $R^7$ are independently hydrido, hydrocarbyl or substituted hydrocarbyl, and $R^2$ and $R^5$ are independently hydrido, halo, hydrocarbyl, or substituted hydrocarbyl or $R^1$ and $R^2$ and/or $R^5$ and $R^6$ may be taken together to form a linkage —Q*—, resulting in a five- or six-membered ring, wherein Q* is —[$(CR^*)_{a^*}$ $(Z)_{b^*}$]— in which a* is 2, 3, or 4, Z is N, O, or S, b* is zero, 1, or 2, the sum of a* and b* is 3 or 4, and R* is selected from the group consisting of hydrido, halo, hydrocarbyl, hydrocarbyloxy, trialkylsilyl, $(NR^8)_2$, $OR^9$, and $NO_2$, wherein $R^8$ and $R^9$ are each independently hydrocarbyl, or wherein R* moieties on adjacent carbon atoms may be linked to form an additional five- or six-membered ring, or $R^2$ and $R^5$ may together form a linkage —Q*— as just defined;

$R^3$ and $R^4$ are independently selected from the group consisting of hydrido and hydrocarbyl;

k, l, m, and n are independently zero or 1;

$Q^1$, $Q^2$, $Q^3$, and $Q^4$ are independently selected from the group consisting of univalent radicals;

$Q^5$ is an optional ligand having the structure of formula (I)

(I)

wherein:

q, X, $R^1$, $R^2$, $R^3$, $R^5$, $R^4$, $R^6$, $R^7$, l, m, and n are as defined above;

$M^1$ is a transition metal;

$M^2$ is a Group IIIA element, a Group IVA element, a Group VA element, a lanthanide, or an actinide;

Q is $J(R^x)_{z-2}$, wherein J is an element with a coordination number of three from Group VB or an element with a coordination number of two from Group VIB, $R^x$ is selected from the group consisting of hydrogen, $C_1$–$C_{24}$ hydrocarbyl, $C_1$–$C_{24}$ hydrocarbyl substituted with one or more halogen atoms, and $C_1$–$C_{24}$ alkoxy, and z is the coordination number of J, and further wherein Q substituents on different L groups are linked through a $C_1$–$C_{24}$ hydrocarbylene bridge;

a is at least 1, b is 0, 1, or 2, and the sum of a and b is 2 or 3;

and a catalyst activator effective to produce a catalytically active ionic species when combined with said complex.

2. The catalyst system of claim 1, wherein the catalyst activator is aluminum-containing or boron-containing.

3. The catalyst system of claim 2, wherein the catalyst activator is aluminum-containing.

4. The catalyst system of claim 3, wherein the catalyst activator is an organoaluminum compound.

5. The catalyst system of claim 4, wherein the catalyst activator is an alkyl aluminoxane.

6. The catalyst system of claim 5, wherein the catalyst activator is methyl aluminoxane.

7. The catalyst system of claim 1, wherein the catalyst activator is boron-containing.

8. The catalyst system of claim 7, wherein the catalyst activator is a fluorohydrocarbylboron compound.

9. The catalyst system of claim 8, wherein the catalyst activator is a fluorinated phenylborate.

10. The catalyst system of claim 1, further including an inert polymerization diluent.

11. The catalyst system of claim 10, wherein the diluent is a volatile hydrocarbon solvent.

12. The catalyst system of claim 1, wherein a is 1 and b is 1.

13. The catalyst system of claim 1, wherein a is 1 and b is 2.

14. The catalyst system of claim 1, wherein a is 2 and b is 0.

15. The catalyst system of claim 1, wherein,

B is a covalent bridging group comprising carbyl, silyl, disilyl, or a $C_1$–$C_{30}$ hydrocarbylene, substituted hydrocarbylene, heterohydrocarbylene, or substituted heterohydrocarbylene radical optionally containing a Group IVB element, a Group VB element, or both;

x is 0, 1, or 2;

y is 0, 1, or 2;

R and R' are independently selected from the group consisting of halogen and $C_1$–$C_{12}$ alkyl, or are ortho to each other and linked to form a cyclopentadienyl or indenyl group;

J is nitrogen, phosphorus, oxygen or sulfur, and $R^x$ is $C_1$–$C_{12}$ alkyl, $C_1$–$C_{12}$ alkyl substituted with a halogen atom, or monocyclic aryl;

$M^1$ is selected from the group consisting of Ti, Hf, Zr, V, Nb, Ta, Cr, Mo, W, Mn, and Re; and X is N and q represents a double bond.

* * * * *